(12) United States Patent
Ji et al.

(10) Patent No.: US 9,339,755 B2
(45) Date of Patent: *May 17, 2016

(54) ETHYLENE SEPARATION WITH TEMPERATURE SWING ADSORPTION

(71) Applicant: Chevron Phillips Chemical Company LP, The Woodlands, TX (US)

(72) Inventors: Lei Ji, Kingwood, TX (US); Ai-Fu Chang, Humble, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/795,784

(22) Filed: Jul. 9, 2015

(65) Prior Publication Data

US 2016/0030878 A1 Feb. 4, 2016

Related U.S. Application Data

(63) Continuation of application No. 14/449,443, filed on Aug. 1, 2014, now Pat. No. 9,126,878.

(51) Int. Cl.
*C08F 2/00* (2006.01)
*C08F 210/00* (2006.01)
(Continued)

(52) U.S. Cl.
CPC ........ *B01D 53/0462* (2013.01); *B01D 53/0407* (2013.01); *B01J 8/085* (2013.01); *B01J 8/087* (2013.01); *B01J 19/00* (2013.01); *C07C 7/12* (2013.01); *C07C 7/13* (2013.01); *C08F 110/02* (2013.01); *B01D 2253/102* (2013.01);
(Continued)

(58) Field of Classification Search
CPC ....... C07C 7/11; C07C 7/005; B01D 53/0462
USPC ..................................................... 526/61, 348
See application file for complete search history.

(56) References Cited

U.S. PATENT DOCUMENTS

| 3,248,179 A | 4/1966 | Norwood |
| 4,501,885 A | 2/1985 | Sherk et al. |

(Continued)

OTHER PUBLICATIONS

Filing receipt and specification for patent application entitled "Ethylene Separation with Temperature Swing Adsorption," by Lei Ji, et al., filed Aug. 1, 2014 as U.S. Appl. No. 14/449,443.

(Continued)

*Primary Examiner* — William Cheung
(74) *Attorney, Agent, or Firm* — Conley Rose, P.C.; Rodney B. Carroll; Monte R. Rhodes

(57) ABSTRACT

A process for component separation in a polymer production system, comprising (a) separating a polymerization product stream into a gas stream and a polymer stream, (b) contacting the polymer stream with a purge gas to yield a purged polymer and a spent purge gas comprising purge gas, ethylene, and ethane, (c) contacting the spent purge gas with a temperature swing adsorber contactor (TSAC) to yield a loaded TSAC, wherein at least a portion of the ethylene is adsorbed by the TSAC at a first temperature to yield TSAC-adsorbed ethylene, wherein a portion of the ethane is adsorbed by the TSAC at the first temperature to yield TSAC-adsorbed ethane, (d) heating the loaded TSAC to a second temperature to yield a regenerated TSAC, and (e) contacting the regenerated TSAC with a sweeping gas stream to yield a recovered adsorbed gas stream comprising sweeping gas, recovered ethylene and recovered ethane.

23 Claims, 4 Drawing Sheets

(51) Int. Cl.
  *B01D 53/04* (2006.01)
  *C07C 7/13* (2006.01)
  *C08F 110/02* (2006.01)
  *B01J 19/00* (2006.01)
  *C07C 7/12* (2006.01)
  *B01J 8/08* (2006.01)

(52) U.S. Cl.
  CPC ..... *B01D2253/108* (2013.01); *B01D 2253/116* (2013.01); *B01D 2253/204* (2013.01); *B01D 2256/24* (2013.01); *B01D 2257/7022* (2013.01); *B01D 2259/40043* (2013.01); *B01J 2208/00212* (2013.01); *B01J 2208/00274* (2013.01); *B01J 2219/0004* (2013.01); *B01J 2219/00837* (2013.01); *B01J 2219/00842* (2013.01); *Y02P 20/582* (2015.11)

(56) References Cited

U.S. PATENT DOCUMENTS

| | | | |
|---|---|---|---|
| 4,727,122 A * | 2/1988 | Lee | C08J 11/02 526/68 |
| 5,455,314 A | 10/1995 | Burns et al. | |
| 5,470,925 A * | 11/1995 | Ramachandran | B01D 53/0462 526/351 |
| 5,565,175 A | 10/1996 | Hottovy et al. | |
| 5,575,979 A | 11/1996 | Hanson | |
| 6,225,421 B1 | 5/2001 | Promel et al. | |
| 6,239,235 B1 | 5/2001 | Hottovy et al. | |
| 6,262,191 B1 | 7/2001 | Hottovy et al. | |
| 6,833,415 B2 | 12/2004 | Kendrick et al. | |
| 7,163,906 B2 | 1/2007 | McDaniel et al. | |
| 7,449,048 B2 * | 11/2008 | Nishida | B01D 53/04 526/77 |
| 8,673,059 B2 | 3/2014 | Leta et al. | |
| 9,126,878 B1 * | 9/2015 | Ji | C07C 7/13 |
| 2007/0197374 A1 | 8/2007 | Yang et al. | |
| 2009/0004417 A1 | 1/2009 | Follestad et al. | |
| 2010/0029872 A1 | 2/2010 | Jensen et al. | |
| 2010/0041842 A1 | 2/2010 | Yang et al. | |

OTHER PUBLICATIONS

Garg, D. R., et al., "The Performance of Molecular Sieve Adsorption Columns: Systems with Micropore Diffusion Control," Chemical Engineering Science, 1974, pp. 571-581, vol. 29, Pergamon Press.

Lively, Ryan P., et al., "Hollow Fiber Adsorbents for CO2 Removal from Flue Gas," Ind. Eng. Chem. Res., 2009, pp. 7314-7324, vol. 48, No. 15, American Chemical Society.

Romero-Pérez, A., et al., "Adsorption Kinetics and Equilibria of Carbon Dioxide, Ethylene, and Ethane on 4A (CECA) Zeolite," J. Chem. Eng. Data, 2010, pp. 3625-3630, vol. 55, No. 9, American Chemical Society.

Notice of Allowance dated May 27, 2015 (14 pages), U.S. Appl. No. 14/449,443, filed Aug. 1, 2014.

* cited by examiner

ETHYLENE SEPARATION WITH TEMPERATURE SWING ADSORPTION

CROSS-REFERENCE TO RELATED APPLICATIONS

This application is a continuation of and claims priority to U.S. patent application Ser. No. 14/449,443 filed on Aug. 1, 2014, now U.S. Pat. No. 9,126,878, and entitled "Ethylene Separation with Temperature Swing Adsorption," which is incorporated by reference herein in its entirety.

TECHNICAL FIELD

The present disclosure generally relates to the production of polyethylene. More specifically, this disclosure relates to a process for improving polyethylene production efficiency by recovering unreacted ethylene.

BACKGROUND

The production of polymers such as polyethylene from light gases requires a high purity feedstock of monomers and comonomers. Due to the small differences in boiling points between the light gases in such a feedstock, industrial production of a high purity feedstock can require the operation of multiple distillation columns, high pressures, and cryogenic temperatures. As such, the energy costs associated with feedstock purification represent a significant proportion of the total cost for the production of such polymers. Further, the infrastructure required for producing, maintaining, and recycling high purity feedstock is a significant portion of the associated capital cost.

In order to offset some of the costs and maximize production, it can be useful to reclaim and/or recycle any unreacted feedstock gases, especially the light hydrocarbon reactants, such as ethylene. Gases comprising unreacted monomers can be separated from the polymer after the polymerization reaction. The polymer is processed while the unreacted monomers are recovered from the gases that are reclaimed following the polymerization reaction. To accomplish this, the reclaimed gas streams have conventionally either been routed through a purification process or redirected through other redundant processing steps. In either case, conventional processes of recovering monomer (e.g., unreacted ethylene) have necessitated energetically unfavorable and expensive processes. Thus, there is an ongoing need for developing efficient processes for the recovery of unreacted ethylene during polyethylene production.

BRIEF SUMMARY

Disclosed herein is a process for component separation in a polymer production system, comprising (a) separating a polymerization product stream into a gas stream and a polymer stream, wherein the polymer stream comprises polyethylene, ethylene and ethane, (b) contacting at least a portion of the polymer stream with a purge gas to yield a purged polymer stream and a spent purge gas stream, wherein the purged polymer stream comprises polyethylene, and wherein the spent purge gas comprises purge gas, ethylene, and ethane, (c) contacting at least a portion of the spent purge gas stream with a temperature swing adsorber contactor (TSAC) to yield a loaded TSAC and a non-adsorbed gas stream, wherein at least a portion of the ethylene is adsorbed by the TSAC at a first temperature to yield TSAC-adsorbed ethylene, wherein a portion of the ethane is adsorbed by the TSAC at the first temperature to yield TSAC-adsorbed ethane, and wherein the loaded TSAC comprises TSAC-adsorbed ethylene and TSAC-adsorbed ethane, (d) heating at least a portion of the loaded TSAC to a second temperature to yield a regenerated TSAC, desorbed ethylene and desorbed ethane, wherein the desorbed ethylene comprises at least a portion of the TSAC-adsorbed ethylene, and wherein the desorbed ethane comprises at least a portion of the TSAC-adsorbed ethane, and (e) contacting at least a portion of the regenerated TSAC with a sweeping gas stream to yield a recovered adsorbed gas stream, wherein the recovered adsorbed gas stream comprises sweeping gas, recovered ethylene and recovered ethane, wherein the recovered ethylene comprises at least a portion of the desorbed ethylene, and wherein the recovered ethane comprises at least a portion of the desorbed ethane.

Further disclosed herein is a process for ethylene recovery from a dilute ethylene stream in a polyethylene production system, comprising (a) providing a dilute ethylene stream comprising ethylene and ethane, wherein a pressure of the dilute ethylene stream is from about 100 kPa to about 150 kPa, wherein ethylene is characterized by a partial pressure of less than about 10 kPa, and wherein ethane is characterized by a partial pressure of less than about 5 kPa, (b) contacting the dilute ethylene stream with a temperature swing adsorber contactor (TSAC) to yield a loaded TSAC and a non-adsorbed gas stream, wherein at least a portion of the ethylene is adsorbed by the TSAC at a first temperature to yield TSAC-adsorbed ethylene, wherein a portion of the ethane is adsorbed by the TSAC at the first temperature to yield TSAC-adsorbed ethane, wherein the loaded TSAC comprises TSAC-adsorbed ethylene and TSAC-adsorbed ethane, and wherein the TSAC is characterized by an adsorption selectivity of ethylene versus ethane at the first temperature of equal to or greater than about 5, (c) heating at least a portion of the loaded TSAC to a second temperature to yield a regenerated TSAC, desorbed ethylene and desorbed ethane, wherein the desorbed ethylene comprises at least a portion of the TSAC-adsorbed ethylene, wherein the desorbed ethane comprises at least a portion of the TSAC-adsorbed ethane, and wherein the second temperature is greater than the first temperature by equal to or greater than about 10° C., and (d) contacting at least a portion of the regenerated TSAC with a sweeping gas stream to yield a recovered adsorbed gas stream, wherein the recovered adsorbed gas stream comprises a sweeping gas, recovered ethylene and recovered ethane, wherein the recovered ethylene comprises at least a portion of the desorbed ethylene, and wherein the recovered ethane comprises at least a portion of the desorbed ethane.

Also disclosed herein is a process for ethylene polymerization, comprising (a) polymerizing ethylene in a slurry loop reactor system to obtain a polymerization product stream, (b) separating a polymerization product stream in a flash chamber into a gas stream and a polymer stream comprising polyethylene, ethylene and ethane, (c) contacting at least a portion of the polymer stream with a purge gas in a purge column to yield a purged polymer stream and a spent purge gas stream, wherein the purged polymer stream comprises polyethylene, and wherein the spent purge gas comprises nitrogen, ethylene, and ethane, (d) contacting at least a portion of the spent purge gas stream with a temperature swing adsorber contactor (TSAC) to yield a loaded TSAC and a non-adsorbed gas stream, wherein at least a portion of the ethylene is adsorbed by the TSAC at a first temperature to yield TSAC-adsorbed ethylene, wherein a portion of the ethane is adsorbed by the TSAC at the first temperature to yield TSAC-adsorbed ethane, wherein the loaded TSAC comprises TSAC-adsorbed ethylene and TSAC-adsorbed ethane, and wherein the TSAC is characterized by an adsorption selectivity of ethylene versus ethane at the first temperature of equal to or greater than about 5, (e) heating at least a portion of the loaded TSAC to a second temperature to yield a regenerated TSAC, desorbed ethylene and desorbed ethane, wherein the desorbed ethylene comprises at least a portion of the TSAC-adsorbed ethylene, wherein the desorbed ethane comprises at least a portion of the TSAC-adsorbed ethane, and wherein the second temperature is greater than the first temperature by equal to or greater than about 10° C., and (f) contacting at least a portion of the regenerated TSAC with olefin-free isobutane to yield a recovered adsorbed gas stream, wherein the recovered adsorbed gas stream comprises isobutane, recovered ethylene and recovered ethane, wherein the recovered ethylene comprises at least a portion of the desorbed ethylene, and wherein the recovered ethane comprises at least a portion of the desorbed ethane.

BRIEF DESCRIPTION OF THE DRAWINGS

For a detailed description of the preferred embodiments of the disclosed processes and systems, reference will now be made to the accompanying drawings in which.

DETAILED DESCRIPTION

Figure 1:
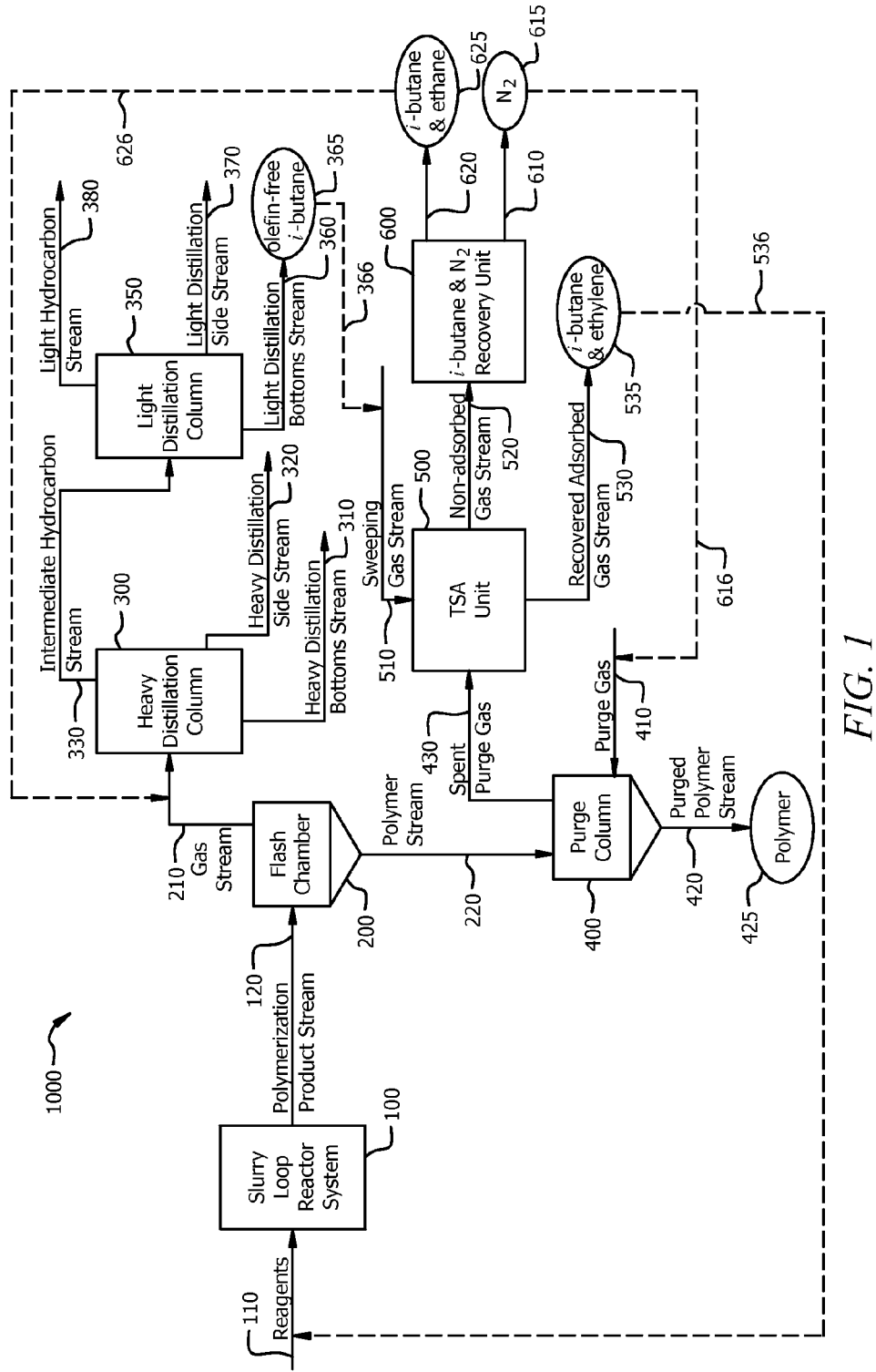
FIG. 1 illustrates a schematic of an embodiment of a polyethylene production system.

It should be understood at the outset that although an illustrative implementation of one or more embodiments are provided below, the disclosed systems and/or methods can be implemented using any number of techniques, whether currently known or in existence. The disclosure should in no way be limited to the illustrative implementations, drawings, and techniques illustrated below, including the exemplary designs and implementations illustrated and described herein, but can be modified within the scope of the appended claims along with their full scope of equivalents.

Disclosed herein are systems, apparatuses, and processes related to petrochemical production processes, for example the production of polyethylene. The systems, apparatuses, and processes are generally related to the separation of a first chemical component or compound (e.g., unreacted monomer, unreacted ethylene) from a composition resulting from petrochemical production processes, for example the production of polyethylene, and comprising the first chemical component or compound and one or more other chemical components, compounds, or the like.

In an embodiment, a process for component separation in a polymer production system (e.g., polyethylene production system) can generally comprise the steps of (a) separating a polymerization product stream into a gas stream and a polymer stream, wherein the polymer stream comprises polyethylene, ethylene (e.g., unreacted ethylene) and ethane; (b) contacting at least a portion of the polymer stream with a purge gas to yield a purged polymer stream and a spent purge gas stream, wherein the purged polymer stream comprises polyethylene, and wherein the spent purge gas comprises purge gas, ethylene, and ethane; (c) contacting at least a portion of the spent purge gas stream with a temperature swing adsorber contactor (TSAC) to yield a loaded TSAC and a non-adsorbed gas stream, wherein at least a portion of the ethylene is adsorbed by the TSAC at a first temperature to yield TSAC-adsorbed ethylene, wherein a portion of the ethane is adsorbed by the TSAC at the first temperature to yield TSAC-adsorbed ethane, and wherein the loaded TSAC comprises TSAC-adsorbed ethylene and TSAC-adsorbed ethane; (d) heating at least a portion of the loaded TSAC to a second temperature to yield a regenerated TSAC, desorbed ethylene and desorbed ethane, wherein the desorbed ethylene comprises at least a portion of the TSAC-adsorbed ethylene, and wherein the desorbed ethane comprises at least a portion of the TSAC-adsorbed ethane; and (e) contacting at least a portion of the regenerated TSAC with a sweeping gas stream to yield a recovered adsorbed gas stream, wherein the recovered adsorbed gas stream comprises sweeping gas, recovered ethylene and recovered ethane, wherein the recovered ethylene comprises at least a portion of the desorbed ethylene, and wherein the recovered ethane comprises at least a portion of the desorbed ethane.

In an embodiment, a process for component separation in a polymer production system (e.g., polyethylene production system) can generally comprise selectively separating a first hydrocarbon (e.g., unreacted monomer, unreacted ethylene) from a second hydrocarbon (e.g., by-product hydrocarbon, by-product ethane), wherein the first hydrocarbon and the second hydrocarbon can be recovered from a polymerization product stream. While the present disclosure will be discussed in detail in the context of a process for selectively separating hydrocarbons in a polyethylene production system, it should be understood that such process or any steps thereof can be applied in any suitable petrochemical production process requiring selective separation of hydrocarbons. The hydrocarbons can comprise any suitable hydrocarbons compatible with the disclosed methods and materials.

Referring to the embodiment of FIG. 1, a polyethylene production (PEP) system 1000 is disclosed. PEP system 1000 generally comprises a slurry loop reactor system 100, a flash chamber 200, a heavy distillation column 300, a light distillation column 350, a purge column 400, a temperature swing adsorption (TSA) unit 500, and an isobutane (i-butane) and nitrogen recovery unit (INRU) 600. In the PEP embodiments disclosed herein, various system components can be in fluid communication via one or more conduits (e.g., pipes, tubing, flow lines, etc.) suitable for the conveyance of a particular stream, for example as shown in detail by the numbered streams in FIG. 1.

In an embodiment, a reagents stream 110 (also referred to as a feed stream) can be communicated to the slurry loop reactor system 100. A polymerization product stream 120 can be communicated from the slurry loop reactor system 100 to the flash chamber 200. A gas stream 210 can be communicated from the flash chamber 200 to the heavy distillation column 300. In some embodiments, the heavy distillation column 300 can be referred to as a first distillation column. A heavy distillation bottoms stream 310 can be emitted from the heavy distillation column 300, and a heavy distillation side stream 320 can be emitted from the heavy distillation column 300. An intermediate hydrocarbon stream 330 can be emitted from the heavy distillation column 300 and communicated to the light distillation column 350. In some embodiments, the light distillation column 350 can be referred to as a second distillation column. A light hydrocarbon stream 380 can be emitted from the light distillation column 350, and a light distillation side stream 370 can be emitted from the light distillation column 350. A light distillation bottoms stream 360 comprising olefin-free isobutane 365 can be emitted from the light distillation column 350. A polymer stream 220 can be communicated from the flash chamber 200 to the purge column 400. A purge gas stream 410 can be communicated to the purge column 400. A purged polymer stream 420 comprising a polymer 425 can be emitted from the purge column 400. A spent purge gas stream 430 can be communicated from the purge column 400 to the TSA unit 500. A sweeping gas stream 510 can be communicated to the TSA unit 500. At least a portion of the olefin-free isobutane 365 can be recycled 366 to the TSA unit 500, for example via the sweeping gas stream 510. A recovered adsorbed gas stream 530 comprising isobutane and ethylene 535 can be emitted from the TSA unit 500. At least a portion of the isobutane and ethylene 535 can be recycled 536 to the slurry loop reactor system 100, for example via the reagents stream 110. A non-adsorbed gas stream 520 can be communicated from the TSA unit 500 to the INRU 600. A gas stream 610 comprising nitrogen 615 can be emitted from the INRU 600. At least a portion of the nitrogen 615 can be recycled 616 to the purge column 400, for example via the purge gas stream 410. A gas stream 620 comprising isobutane and ethane 625 can be emitted from the INRU 600. At least a portion of the isobutane and ethane 625 can be recycled to one or more distillation columns. For example, at least a portion of the isobutane and ethane 625 can be recycled 626 to the heavy distillation column 300, for example via the gas stream 210.

For purposes of the disclosure herein an "olefin-free" hydrocarbon (e.g., olefin-free isobutane) refers to a hydrocarbon (e.g., isobutane) that can be free of olefins, alternatively, substantially free of olefins, alternatively, essentially free of olefins, or alternatively, consist or consist essentially of non-olefins. For example, olefins can be present in an olefin-free hydrocarbon (e.g., olefin-free isobutane) in an amount of less than about 10% by total weight of the olefin-free hydrocarbon, alternatively, less than about 9%, alternatively, less than about 8%, alternatively, less than about 7%, alternatively, less than about 6%, alternatively, less than about 5%, alternatively, less than about 4%, alternatively, less than about 3%, alternatively, less than about 2%, alternatively, less than about 1.0%, alternatively, less than about 0.5%, alternatively, less than about 0.1%.

Embodiments of a suitable PEP system having been disclosed, embodiments of a PEP process are now disclosed. One or more of the embodiments of a PEP process can be described with reference to one or more embodiments of PEP system 1000. Although a given PEP process can be described with reference to one or more embodiments of a PEP system, such a disclosure should not be construed as so-limiting. Although the various steps of the processes disclosed herein may be disclosed or illustrated in a particular order, such should not be construed as limiting the performance of these processes to any particular order unless otherwise indicated.

Figure 2:
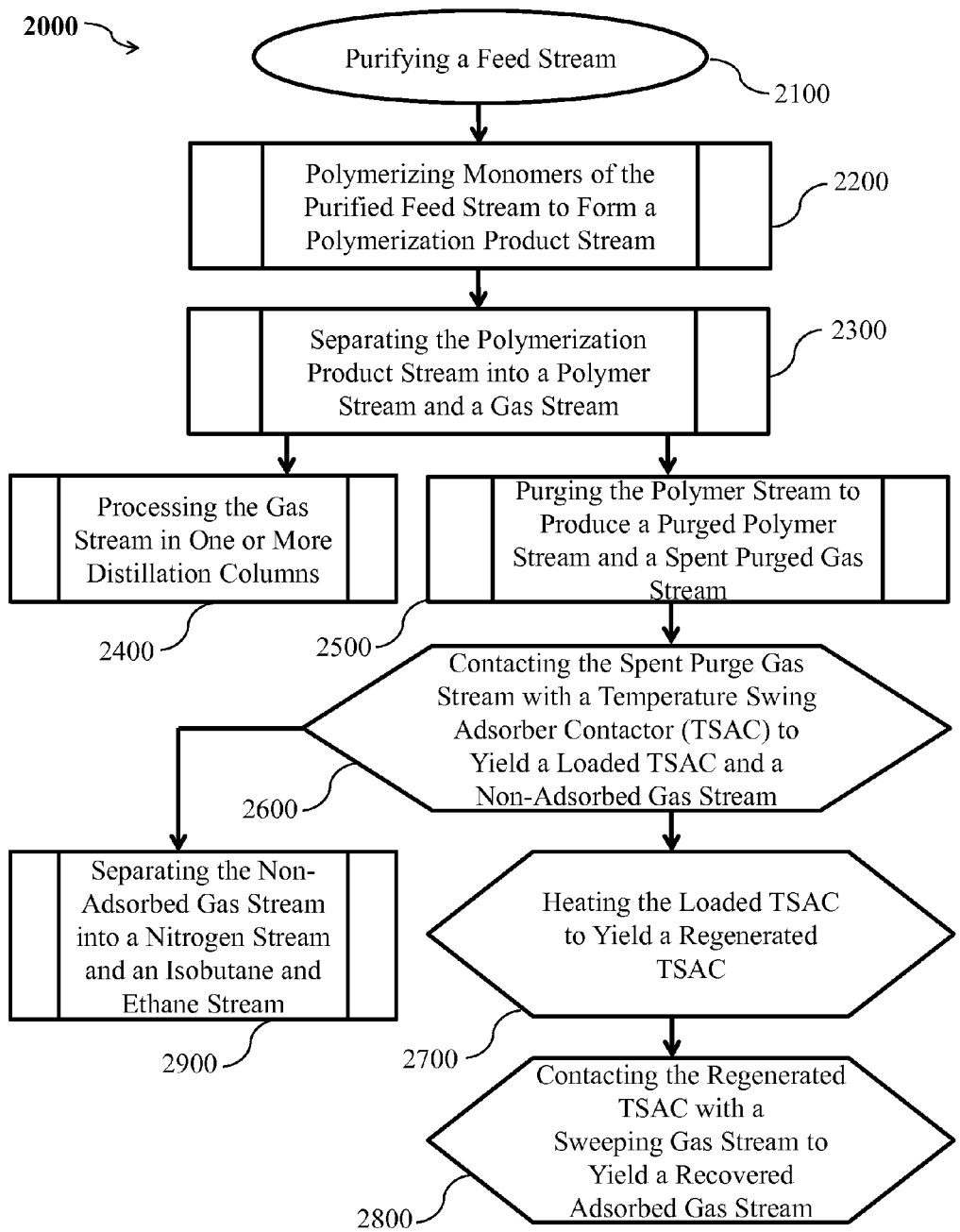
FIG. 2 illustrates a flow diagram of an embodiment of a polyethylene production process.

Referring to the embodiment of FIG. 2, a PEP process 2000 is illustrated. PEP process 2000 can generally comprise (i) a step 2100 of purifying a feed stream; (ii) a step 2200 of polymerizing monomers of the purified feed stream to form a polymerization product stream; (iii) a step 2300 of separating the polymerization product stream into a polymer stream and a gas stream; (iv) a step 2400 of processing the gas stream in one or more distillation columns; (v) a step 2500 of purging the polymer stream to produce a purged polymer stream and a spent purge gas stream; (vi) a step 2600 of contacting the spent purge gas stream with a temperature swing adsorber contactor (TSAC) to yield a loaded TSAC and a non-adsorbed gas stream; (vii) a step 2700 of heating the loaded TSAC to yield a regenerated TSAC; (viii) a step 2800 of contacting the regenerated TSAC with a sweeping gas stream to yield a recovered adsorbed gas stream; and (ix) a step 2900 of separating the non-adsorbed gas stream into a nitrogen stream and an isobutane and ethane stream.

In an embodiment, the PEP process 2000 or a portion thereof can be implemented via the PEP system 1000 (e.g., as illustrated in FIG. 1).

In an embodiment, the PEP process 2000 can generally comprise the step 2100 of purifying a feed stream or a reagents stream. In one or more of the embodiments disclosed herein, purifying a feed stream can comprise separating unwanted compounds and elements from a feed stream comprising ethylene to form a purified feed stream. In an embodiment, purifying a feed stream can comprise any suitable method or process, including the non-limiting examples of filtering, membrane screening, reacting with various chemicals, absorbing, adsorbing, distillation(s), or combinations thereof.

Figure 3:
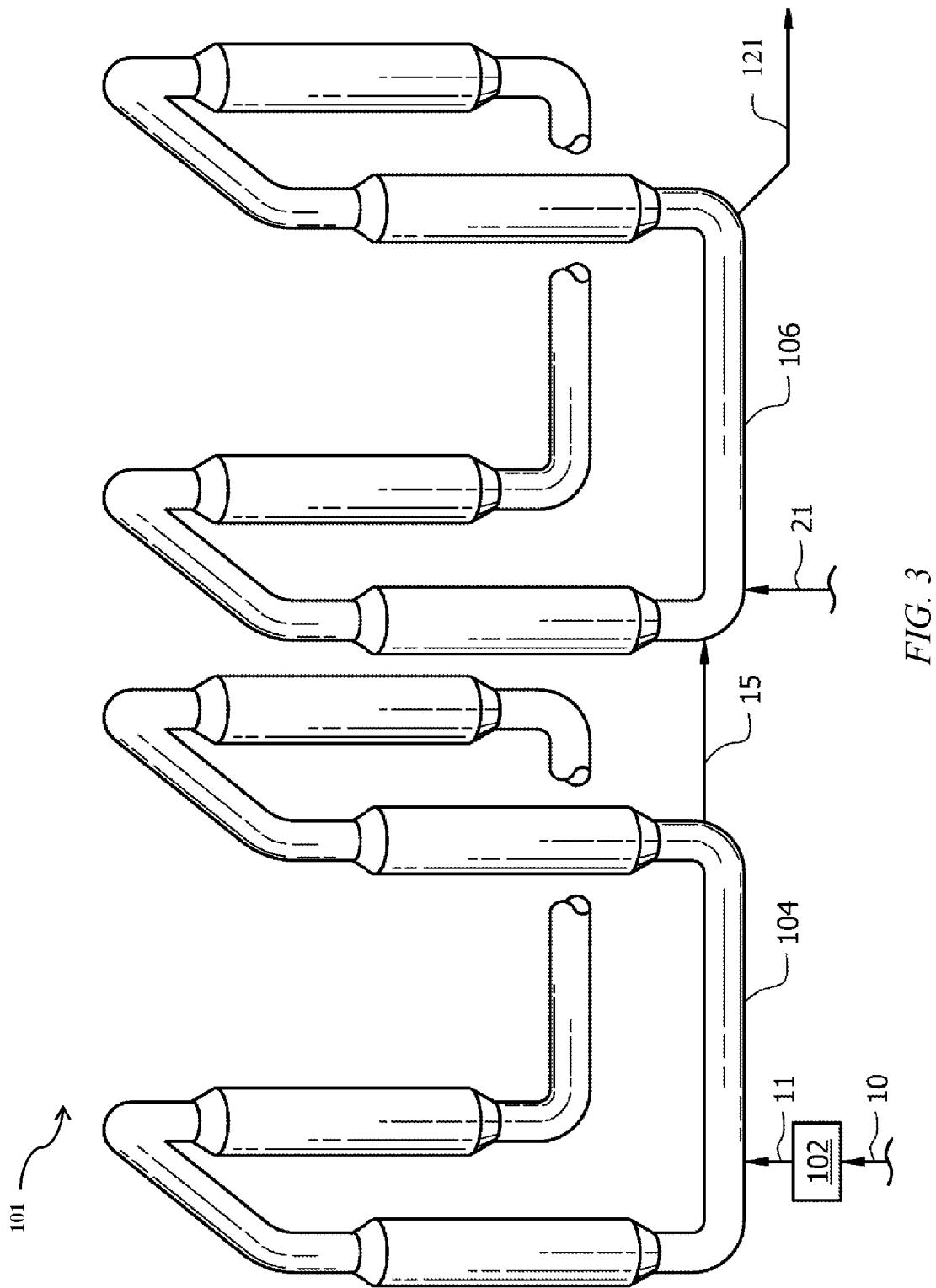
FIG. 3 illustrates a schematic of an embodiment of a slurry loop reactor system.

Referring to the embodiment of FIG. 3, a feed stream 10 (e.g., reagents stream 110 in the embodiment of FIG. 1) can be communicated to a purifier 102. In an embodiment, the feed stream 10 can comprise ethylene and various other gases, such as but not limited to methane, ethane, acetylene, propane, propylene, water, nitrogen, oxygen, various other gaseous hydrocarbons having three or more carbon atoms, various contaminants, or combinations thereof. In one or more of the embodiments disclosed herein, the purifier 102 can comprise a device or apparatus suitable for the purification of one or more reactant gases in a feed stream comprising a plurality of potentially unwanted gaseous compounds, elements, contaminants, and the like. Non-limiting examples of a suitable purifier 102 can comprise a filter, a membrane, a reactor, an absorbent, a molecular sieve, one or more distillation columns, or combinations thereof. The purifier 102 can be configured to separate ethylene from a stream comprising a plurality of potentially unwanted gaseous compounds, elements, contaminants, and the like.

In an embodiment, purifying a feed stream can yield a purified feed stream 11 comprising substantially pure monomers (e.g., substantially pure ethylene). In an embodiment, the purified feed stream can comprise less than about 25% by total weight of the stream, alternatively, less than about 10%, alternatively, less than about 1.0% of any one or more of nitrogen, oxygen, methane, ethane, propane, comonomers, or combinations thereof. As used herein "substantially pure ethylene" refers to a fluid stream comprising at least about 60% ethylene, alternatively, at least about 70% ethylene, alternatively, at least about 80% ethylene, alternatively, at least about 90% ethylene, alternatively, at least about 95% ethylene, alternatively, at least about 99% ethylene by total weight of the stream, alternatively, at least about 99.5% ethylene by total weight of the stream. In an embodiment, the feed stream 11 can further comprise trace amounts of ethane, for example, as from a recycled stream, as will be discussed in more detail later herein.

In some embodiments, the purified feed stream can comprise a comonomer, such as unsaturated hydrocarbons having from 3 to 20 carbon atoms. Nonlimiting examples of comonomers that can be present in the purified feed stream include alpha olefins, such as for example propylene, 1-butene, 1-pentene, 1-hexene, 3-methyl-1-butene, 4-methyl-1-pentene, 1-heptene, 1-octene, 1-nonene, 1-decene, and the like, or combinations thereof.

In an embodiment, the PEP process 2000 can generally comprise the step 2200 of polymerizing monomers of the purified feed stream to form a polymerization product stream.

The polymerization product stream can be formed using any suitable olefin polymerization method which can be carried out using various types of polymerization reactors.

As used herein, the terms "polymerization reactor" or "reactor" include any polymerization reactor capable of polymerizing olefin monomers or comonomers to produce homopolymers or copolymers. Such homopolymers and copolymers are referred to as resins or polymers. The various types of reactors include those that can be referred to as batch, slurry, tubular or autoclave reactors. Slurry reactors can comprise vertical or horizontal loops. Reactor types can include batch or continuous processes. Continuous processes could use intermittent or continuous product discharge. Processes can also include partial or full direct recycle of unreacted monomer, unreacted comonomer, and/or diluent.

Polymerization reactor systems of the present disclosure can comprise one type of reactor in a system or multiple reactors of the same or different type. Production of polymers in multiple reactors can include several stages in at least two separate polymerization reactors interconnected by transfer stream(s), line(s), apparatus(es) (for example, a separation vessel(s)) and/or device(s) (for example, a valve or other mechanism) making it possible to transfer the polymers resulting from a first polymerization reactor into a second reactor. The desired polymerization conditions in one of the reactors can be different from the operating conditions of the other reactors. Alternatively, polymerization in multiple reactors can include the manual transfer of polymer from one reactor to subsequent reactors for continued polymerization. Multiple reactor systems can include any combination including, but not limited to, multiple loop reactors. The multiple reactors can be operated in series or in parallel.

According to one aspect of this disclosure, the polymerization reactor system can comprise at least one loop slurry reactor comprising vertical or horizontal loops. Monomer, diluent, catalyst, and optionally any comonomer can be continuously fed to a loop reactor where polymerization occurs. Generally, continuous processes can comprise the continuous introduction of a monomer, an optional comonomer, a catalyst, and a diluent into a polymerization reactor and the continuous removal from this reactor of a suspension comprising polymer particles and the diluent. Reactor effluent can be flashed to remove the solid polymer from the liquids that comprise the diluent, monomer and/or comonomer. Various technologies can be used for this separation step including but not limited to, flashing that can include any combination of heat addition and pressure reduction; separation by cyclonic action in either a cyclone or hydrocyclone; or separation by centrifugation.

A suitable slurry polymerization process (also known as the particle form process), is disclosed, for example, in U.S. Pat. Nos. 3,248,179; 4,501,885; 5,565,175; 5,575,979; 6,239,235; 6,262,191; and 6,833,415; each of which is incorporated by reference herein in its entirety.

In one or more embodiments, suitable diluents used in slurry polymerization include, but are not limited to, the monomer, and optionally, the comonomer, being polymerized and hydrocarbons that are liquids under reaction conditions. Examples of suitable diluents include, but are not limited to, hydrocarbons such as propane, cyclohexane, isobutane, n-butane, n-pentane, isopentane, neopentane, and n-hexane. Some loop polymerization reactions can occur under bulk conditions where no diluent is used. An example is polymerization of propylene monomer as disclosed in U.S. Pat. No. 5,455,314, which is incorporated by reference herein in its entirety.

Polymerization reactors suitable for the disclosed systems and processes can further comprise any combination of at least one raw material feed system, at least one feed system for catalyst or catalyst components, and/or at least one polymer recovery system. Suitable reactor systems can further comprise systems for feedstock purification, catalyst storage and preparation, extrusion, reactor cooling, polymer recovery, fractionation, recycle, storage, loadout, laboratory analysis, and process control.

Conditions (e.g., polymerization conditions) that are controlled for polymerization efficiency and to provide resin properties include temperature, pressure, type and/or quantity of catalyst or co-catalyst, and concentrations and/or partial pressures of various reactants.

Polymerization temperature can affect catalyst productivity, polymer molecular weight and molecular weight distribution. Suitable polymerization temperature can be any temperature below the de-polymerization temperature according to the Gibbs Free energy equation. Typically this includes from about 60° C. to about 280° C., for example, and from about 70° C. to about 110° C., depending upon the type of polymerization reactor.

Suitable pressures will also vary according to the reactor and polymerization type. The pressure for liquid phase polymerizations in a loop reactor is typically less than about 1,000 psig. Polymerization reactors can also be operated in a supercritical region occurring at generally higher temperatures and pressures. Operation above the critical point of a pressure/temperature diagram (supercritical phase) can offer advantages. In an embodiment, polymerization can occur in an environment having a suitable combination of temperature and pressure. For example, polymerization can occur at a pressure in a range of from about 550 psi to about 650 psi, alternatively, from about 600 psi to about 625 psi and a temperature in a range of from about 170° F. to about 230° F., alternatively, from about 195° F. to about 220° F.

The concentration of various reactants can be controlled to produce resins with certain physical and mechanical properties. The proposed end-use product that will be formed by the resin and the method of forming that product determines the desired resin properties. Mechanical properties include tensile, flexural, impact, creep, stress relaxation and hardness tests. Physical properties include density, molecular weight, molecular weight distribution, melting temperature, glass transition temperature, temperature melt of crystallization, density, stereoregularity, crack growth, long chain branching and rheological parameters.

The concentrations and/or partial pressures of monomer, comonomer, hydrogen, co-catalyst, modifiers, and electron donors are important in producing these resin properties. Comonomer can be used to control product density. Hydrogen can be used to control product molecular weight. Cocatalysts can be used to alkylate, scavenge poisons and control molecular weight. Modifiers can be used to control product properties and electron donors affect stereoregularity, the molecular weight distribution, or molecular weight. In addition, the concentration of poisons is minimized because poisons impact the reactions and product properties.

In an embodiment, any suitable catalyst system can be employed. A suitable catalyst system can comprise a catalyst and, optionally, a co-catalyst (e.g., organoaluminum compound) and/or promoter. Non-limiting examples of suitable catalyst systems include Ziegler Natta catalysts, Ziegler catalysts, chromium catalysts, chromium oxide catalysts, chromocene catalysts, metallocene catalysts, nickel catalysts, or combinations thereof. Catalyst systems suitable for use in the present disclosure have been described, for example, in U.S.

Pat. No. 7,619,047 and U.S. Patent Application Publication Nos. 2007/0197374, 2009/0004417, 2010/0029872, 2006/0094590, and 2010/0041842, each of which is incorporated by reference herein in its entirety.

In an embodiment of the present disclosure, the catalyst system can comprise an activator. The activator can be a solid oxide activator-support, a chemically treated solid oxide, a clay mineral, a pillared clay, an exfoliated clay, an exfoliated clay gelled into another oxide matrix, a layered silicate mineral, a non-layered silicate mineral, a layered aluminosilicate mineral, a non-layered aluminosilicate mineral, an aluminoxane, a supported aluminoxane, an ionizing ionic compound, an organoboron compound, or any combination thereof. The terms "chemically-treated solid oxide," "solid oxide activator-support," "acidic activator-support," "activator-support," "treated solid oxide compound," and the like are used herein to indicate a solid, inorganic oxide of relatively high porosity, which exhibits Lewis acidic or Brønsted acidic behavior, and which has been treated with an electron-withdrawing component, typically an anion, and which is calcined. The electron-withdrawing component is typically an electron-withdrawing anion source compound. Thus, the chemically-treated solid oxide compound comprises the calcined contact product of at least one solid oxide compound with at least one electron-withdrawing anion source compound. Typically, the chemically-treated solid oxide comprises at least one ionizing, acidic solid oxide compound. The terms "support" and "activator-support" are not used to imply these components are inert, and such components should not be construed as an inert component of the catalyst composition.

In one or more of the embodiments disclosed herein, monomers in a feed stream (e.g., purified feed stream 11) can be polymerized. In one or more embodiments, polymerizing monomers of the purified feed stream can comprise allowing a polymerization reaction between a plurality of monomers by contacting a monomer or monomers with a catalyst system under conditions suitable for the formation of a polymer. In one or more of the embodiments disclosed herein, polymerizing comonomers of the purified feed stream can comprise allowing a polymerization reaction between a plurality of comonomers by contacting a comonomer or comonomers with a catalyst system under conditions suitable for the formation of a copolymer.

In an aspect of this disclosure, the step 2200 of polymerizing monomers of the purified feed stream to form a polymerization product stream can be carried out using a slurry loop reactor system, such as for example a slurry loop reactor system 101 illustrated in the embodiment of FIG. 3. The slurry loop reactor system 101 generally comprises a purifier 102, a first reactor 104, and a second reactor 106. In the slurry loop reactor system embodiments disclosed herein, various system components can be in fluid communication via one or more conduits (e.g., pipes, tubing, flow lines, etc.) suitable for the conveyance of a particular stream, for example as shown in detail by the numbered streams in FIG. 3.

In an embodiment, a purified feed stream 11 can be communicated from the purifier 102 to one or more of the reactors (e.g., a first reactor 104, a second reactor 106). Where the slurry loop reactor system comprises two or more reactors, a mid-polymerization reactor stream 15 can be communicated from the first reactor 104 to the second reactor 106. Hydrogen can be introduced into the second reactor 106 in stream 21. A polymerization product stream (e.g., polymerization product stream 121 in FIG. 3, polymerization product stream 120 in FIG. 1) can be emitted from the first reactor 104 and/or the second reactor 106.

In embodiments as illustrated by FIG. 3, polymerizing monomers of the purified feed stream can comprise routing the purified feed stream 11 to the one or more of the polymerization reactors 104, 106. Polymerizing monomers of the mid-polymerization reactor stream 15 can comprise routing the mid-polymerization reactor stream 15 to polymerization reactor(s) 106. In embodiments as illustrated by FIG. 3, polymerizing monomers of the mid-polymerization reactor stream 15 can comprise routing the mid-polymerization reactor stream 15 from polymerization reactor(s) 104 to polymerization reactor(s) 106.

In one or more of the embodiments disclosed herein, the polymerization reactors 104, 106 can comprise any vessel or combination of vessels suitably configured to provide an environment for a chemical reaction (e.g., a contact zone) between monomers (e.g., ethylene) and/or polymers (e.g., an "active" or growing polymer chain), and optionally comonomers and/or copolymers, in the presence of a catalyst to yield a polymer (e.g., a polyethylene polymer) and/or copolymer. Although the embodiments illustrated in FIG. 3 illustrate a PEP system having two reactors in series, one of skill in the art viewing this disclosure will recognize that one reactor, alternatively, any suitable number and/or configuration of reactors, can be employed.

In embodiments as illustrated in FIG. 3, production of polymers in multiple reactors can include at least two polymerization reactors 104, 106 interconnected by one or more devices or apparatus (e.g., valve, continuous take-off valve, and/or continuous take-off mechanism). In embodiments as illustrated in FIG. 3, production of polymers in multiple reactors can include at least two polymerization reactors 104, 106 interconnected by one or more streams or lines (e.g., mid-polymerization reactor stream 15). In some embodiments, production of polymers in multiple reactors can include at least two polymerization reactors 104, 106 interconnected by one or more separators (e.g., flash chambers).

In an embodiment, polymerizing monomers can comprise introducing a suitable catalyst system into the first and/or second reactor 104, 106, respectively, so as to form a slurry. Alternatively, a suitable catalyst system can reside in the first and/or second reactor 104, 106, respectively.

As previously described herein, polymerizing monomers can comprise selectively manipulating one or more polymerization reaction conditions to yield a given polymer product, to yield a polymer product having one or more desirable properties, to achieve a desired efficiency, to achieve a desired yield, the like, or combinations thereof. In an embodiment, polymerizing monomers of the purified feed stream 11 can comprise adjusting one or more polymerization reaction conditions.

In an embodiment, polymerizing monomers can comprise maintaining a suitable temperature, pressure, and/or partial pressure(s) during the polymerization reaction, alternatively, cycling between a series of suitable temperatures, pressures, and/or partial pressure(s) during the polymerization reaction.

In an embodiment, polymerizing monomers can comprise polymerizing comonomers in one or more of polymerization reactors 104, 106. In an embodiment, polymerizing monomers can comprise introducing ethylene monomer and/or a comonomer to the polymerization reactor 106.

In an embodiment, polymerizing monomers can include introducing hydrogen into one or more of reactors 104 and 106. For example, FIG. 3 illustrates hydrogen can be introduced into reactor 106 through stream 21. The amount of hydrogen introduced into the reactor 106 can be adjusted so as to obtain, in the diluent, a molar ratio of hydrogen to ethylene of 0.001 to 0.1. This molar ratio can be at least 0.004 in reactor

106. In some embodiments, this molar ratio cannot exceed 0.05. The ratio of the concentration of hydrogen in the diluent in reactor 104 to the concentration of hydrogen polymerization reactor 106 can be at least 20, alternatively, at least 30, alternatively, at least 40, alternatively, not greater than 300, alternatively, not greater than 200. Suitable hydrogen concentration control methods and systems are disclosed in U.S. Pat. No. 6,225,421, which is incorporated by reference herein in its entirety.

In an embodiment, polymerizing monomers can comprise circulating, flowing, cycling, mixing, agitating, or combinations thereof, the monomers (optionally, comonomers), catalyst system, and/or the slurry within and/or between the reactors 104, 106. In an embodiment where the monomers (optionally, comonomers), catalyst system, and/or slurry are circulated, circulation can be at a velocity (e.g., slurry velocity) of from about 1 m/s to about 30 m/s, alternatively, from about 2 m/s to about 17 m/s, or alternatively, from about 3 m/s to about 15 m/s.

In some embodiments, polymerizing monomers can comprise configuring reactors 104, 106 to yield an unimodal resin. Herein, the "modality" of a polymer resin refers to the form of its molecular weight distribution curve, i.e., the appearance of the graph of the polymer weight fraction as a function of its molecular weight. The polymer weight fraction refers to the weight fraction of molecules of a given size. A polymer having a molecular weight distribution curve showing a single peak can be referred to as a unimodal polymer, a polymer having curve showing two distinct peaks can be referred to as bimodal polymer, a polymer having a curve showing three distinct peaks can be referred to as trimodal polymer, etc.

In other embodiments, polymerizing monomers can comprise configuring reactors 104, 106 to yield a multimodal (e.g., a bimodal) polymer (e.g., polyethylene). For example, the resultant polymer can comprise both a relatively high molecular weight, low density (HMWLD) polyethylene polymer and a relatively low molecular weight, high density (LMWHD) polyethylene polymer. For example, various types of suitable polymers can be characterized as having a various densities. For example, a Type I can be characterized as having a density in a range of from about 0.910 g/cm$^3$ to about 0.925 g/cm$^3$, alternatively, a Type II can be characterized as having a density from about 0.926 g/cm$^3$ to about 0.940 g/cm$^3$, alternatively, a Type III can be characterized as having a density from about 0.941 g/cm$^3$ to about 0.959 g/cm$^3$, alternatively, a Type IV can be characterized as having a density of greater than about 0.960 g/cm$^3$.

In the embodiments illustrated in FIG. 3, polymerizing monomers of the purified feed stream 11 can yield polymerization product stream 121. In an embodiment, the polymerization product stream 121 (e.g., polymerization product stream 120 in FIG. 1) can generally comprise various solids, semi-solids, volatile and nonvolatile liquids, gases and combinations thereof. Polymerizing monomers of the purified feed stream 11 can yield the polymerization product stream 121 generally comprising unreacted monomer (e.g., ethylene), optional unreacted comonomer, by-products (e.g., ethane, which can be by-product ethane formed from ethylene and hydrogen), and a polymerization product (e.g., polymer and optionally, copolymer). As used herein, an "unreacted monomer," for example, ethylene, refers to a monomer that was introduced into a polymerization reactor during a polymerization reaction but was not incorporated into a polymer. As used herein, an "unreacted comonomer" refers to a comonomer that was introduced into a polymerization reactor during a polymerization reaction but was not incorporated into a polymer. The solids and/or liquids of the polymerization product stream 121 can comprise a polymer product (e.g., a polyethylene polymer), often referred to at this stage of the PEP process as "polymer fluff." The gases of the polymerization product stream 121 can comprise unreacted, gaseous reactant monomers or optional comonomers (e.g., unreacted ethylene monomers, unreacted comonomers), gaseous waste products, gaseous contaminants, or combinations thereof.

In an embodiment, the polymerization product stream 121 can comprise hydrogen, nitrogen, methane, ethylene, ethane, propylene, propane, butane, 1-butene, isobutane, pentane, hexane, 1-hexene and heavier hydrocarbons. In an embodiment, ethylene can be present in a range of from about 0.1% to about 15%, alternatively, from about 1.5% to about 5%, alternatively, about 2% to about 4% by total weight of the polymerization product stream. Ethane can be present in a range of from about 0.001% to about 4%, alternatively, from about 0.2% to about 0.5% by total weight of the polymerization product stream. Isobutane can be present in a range from about 80% to about 98%, alternatively, from about 92% to about 96%, alternatively, about 95% by total weight of the polymerization product stream.

In an embodiment, the PEP process 2000 can generally comprise the step 2300 of separating the polymerization product stream into a polymer stream and a gas stream. In one or more of the embodiments disclosed herein, separating the polymerization product into a polymer stream and a gas stream can generally comprise removing gases from liquids and/or solids (e.g., the polymer fluff) by any suitable process.

In embodiments as illustrated by FIG. 1, separating the polymerization product into a polymer stream and a gas stream can comprise routing the polymerization product stream 120 to a separator (e.g., flash chamber 200). In some embodiments, the polymerization product stream 120 can comprise at least a portion of the polymerization product stream 121 emitted from the second reactor 106. In other embodiments, the polymerization product stream 120 can comprise at least a portion of the mid-polymerization reactor stream 15 emitted from the first reactor 104. In yet other embodiments, the polymerization product stream 120 can comprise at least a portion of the polymerization product stream 121 and at least a portion of the mid-polymerization reactor stream 15.

In one or more of the embodiments disclosed herein, a separator such as flash chamber 200 can be configured to separate a stream (e.g., polymerization product stream 120 comprising polyethylene) into gases, liquids, solids, or combinations thereof.

In an embodiment, the separator for separating the polymerization product stream into a polymer stream and a gas stream can comprise a vapor-liquid separator. As will be appreciated by one of skill in the art, and with the help of this disclosure, the solids of the polymerization product stream (e.g., polymer fluff) are slurried in the liquids of the polymerization product stream, and a vapor-liquid separator would generally separate the solids and the liquid in a single slurry phase from the gases of the polymerization product stream. Nonlimiting examples of separators suitable for use in the present disclosure a fixed-bed adsorption column, a flash tank, a filter, a membrane, a reactor, an absorbent, an adsorbent, a molecular sieve, or combinations thereof.

In an embodiment, the separator comprises a flash tank (e.g., flash chamber 200). Without wishing to be limited by theory, such a flash tank can comprise a vessel configured to vaporize and/or remove low vapor pressure components from a high temperature and/or high pressure fluid. The separator for separating the polymerization product into a polymer stream and a gas stream can be configured such that an incoming stream can be separated into a liquid stream (e.g., a condensate stream) and a gas (e.g., vapor) stream. The liquid stream can comprise a reaction product (e.g., polyethylene, often referred to as "polymer fluff"). The liquid stream can be a bottoms stream. The gas or vapor stream can comprise volatile solvents, gaseous, unreacted monomers and/or optional comonomers, waste gases (secondary reaction products, such as contaminants and the like), or combinations thereof. The gas stream can be an overhead stream.

The separator for separating the polymerization product into a polymer stream and a gas stream can be configured such that the polymerization product stream is flashed by heat, pressure reduction, or both such that an enthalpy of the polymerization product stream is increased. This can be accomplished via a heater, a flashline heater, various other operations commonly known in the art, or combinations thereof. For example, a flash line heater comprising a double pipe can exchange heat by hot water or steam. Such a flashline heater can increase the temperature of the stream while reducing its pressure.

In one or more embodiments, separating the polymerization product stream into a polymer stream and a gas stream can comprise distilling, vaporizing, flashing, filtering, membrane screening, centrifuging, absorbing, adsorbing, or combinations thereof, the polymerization product. In the embodiments illustrated in FIG. 1, separating the polymerization product stream into a polymer stream and a gas stream yields a gas stream 210 and a polymer stream 220 (e.g., polyethylene polymer, copolymer).

In an embodiment, the gas stream 210 can comprise unreacted monomer (e.g., unreacted ethylene monomer), optional unreacted comonomer, and various gases. Gas stream 210 can comprise the non-solid components of polymerization product stream 120 in a vapor phase. In an embodiment, the gas stream 210 can comprise hydrogen, nitrogen, methane, ethylene, ethane, propylene, propane, butane, isobutane, pentane, hexane, 1-hexene, heavier hydrocarbons, or combinations thereof. In an embodiment, the gas stream 210 can further comprise trace amounts of oxygen. In an embodiment, ethylene can be present in a range of from about 0.1% to about 15%, alternatively, from about 1.5% to about 5%, alternatively, about 2% to about 4% by total weight of the gas stream. Ethane can be present in a range of from about 0.001% to about 4%, alternatively, from about 0.2% to about 0.5% by total weight of the gas stream. Isobutane can be present in a range from about 80% to about 98%, alternatively, from about 92% to about 96%, alternatively, about 95% by total weight of the gas stream.

In some embodiments, the mid-polymerization reactor stream 15 can be processed in a similar manner to the polymerization product stream 121, wherein the mid-polymerization reactor stream 15 can be separated into a mid-polymerization polymer stream and a mid-polymerization gas stream. In such embodiments, the mid-polymerization polymer stream can be communicated to the second reactor 106; processed in a similar manner to the polymer stream 220, as will be described in more detail later herein; communicated to the purge column 400, such as for example via the polymer stream 220; or combinations thereof. In such embodiments, the mid-polymerization gas stream can be processed in a similar manner to the gas stream 210, as will be described in more detail later herein, and/or communicated to the heavy distillation column 300, such as for example via the gas stream 210.

In an embodiment, the PEP process 2000 can generally comprise the step 2400 of processing the gas stream in one or more distillation columns. In an embodiment, processing the gas stream 210 can comprise separating at least one gaseous component from the gas stream. While the step of processing the gas stream will be discussed in detail in the context of two distillation columns used for such processing of the gas stream, it should be understood that any suitable number of distillation columns can be used for processing the gas stream, such as for example one, two, three, four, five, or more distillation columns.

In an embodiment, separating at least one gaseous component from the gas stream can comprise distilling a gas stream (e.g., gas stream 210) in one step so as to allow at least one gaseous component to separate from other gaseous components according to temperature(s) of boiling. In such an embodiment, separating at least one gaseous component from the gas stream can comprise distilling a gas stream into a light hydrocarbon stream comprising ethylene, ethane, optionally hydrogen, or combinations thereof. In such an embodiment, separating at least one gaseous component from the gas stream can comprise collecting hexane, hexene, optionally isobutane, or combinations thereof in a distillation bottoms stream. In an additional and/or alternative embodiment, separating at least one gaseous component from the gas stream can comprise collecting isobutane from a side stream and/or a distillation bottoms stream of a distillation column.

In the embodiment of the PEP system 1000 shown in FIG. 1, distillation columns 300 and 350 can be configured to separate at least one gaseous component from a gas stream (e.g., gas stream 210). Processing the gas stream 210 in one or more distillation columns can yield several hydrocarbon fractions. The gas stream 210 can be communicated to the heavy distillation column 300. Gas stream 210 can be distilled in the heavy distillation column 300 to form intermediate hydrocarbon stream 330 which can be communicated to the light distillation column 350. Non-distilled components in the heavy distillation column 300 can emit from the heavy distillation column 300 in heavy distillation bottoms stream 310. Heavy distillation side stream 320 can optionally emit from the heavy distillation column 300.

Intermediate hydrocarbon stream 330 can be characterized as comprising, alternatively, comprising substantially, alternatively, consisting essentially of, alternatively, consisting of, $C_4$ and lighter hydrocarbons (e.g., butane, isobutane, propane, ethane, or methane) and any light gases (e.g., nitrogen). For example, $C_4$ and lighter hydrocarbons and gases can be present in the intermediate hydrocarbon stream 330 in an amount of from about 80% to about 100% by total weight of the intermediate hydrocarbon stream, alternatively from about 90% to about 99.999999%, alternatively from about 99% to about 99.9999%, alternatively, $C_5$ and heavier hydrocarbons can be present in the intermediate hydrocarbon stream 330 in an amount from about 0% to about 20% by total weight of the intermediate hydrocarbon stream, alternatively from about 10% to about 0.000001%, alternatively from about 1.0% to about 0.0001%. Also, for example, at least 90% by weight of the $C_4$ and lighter hydrocarbons and gases of the gas stream 210 can be present in the intermediate hydrocarbon stream 330, alternatively, at least 98%, alternatively, at least 99%.

In an embodiment, heavy distillation bottoms stream 310 can be characterized as comprising $C_6$ and heavy components, wherein the heavy components can comprise alkanes, that is, alkanes larger than hexane (e.g., heptane and/or other large alkanes). In an embodiment, hydrocarbons other than $C_6$ and heavy alkanes can be present in the heavy distillation bottoms stream 310 in an amount less than about 15%, alternatively, less than about 10%, alternatively, less than about 5% by total weight of the heavy distillation bottoms stream 310. In an embodiment, the heavy distillation bottoms stream 310 can be directed to additional processing steps or methods, or alternatively they can be disposed of, as appropriate. In an embodiment, heavy distillation bottoms stream 310 can be incinerated.

In an embodiment, heavy distillation side stream 320 can be characterized as comprising hexene. For example, hexene can be present in heavy distillation side stream 320 in an amount of from about 20% to about 98% by total weight of the heavy distillation side stream 320, alternatively from about 40% to about 95%, alternatively from about 50% to about 95%.

In an embodiment, the heavy distillation side stream 320 can be recycled. In an embodiment, recycling the heavy distillation side stream 320 can comprise routing, for example, via a suitable pump or compressor, the heavy distillation side stream 320 back to and/or introducing the heavy distillation side stream 320 into one or more components of the PEP system 1000, for example, into slurry loop reactor system 100 for reuse in a polymerization reaction. Recycling the heavy distillation side stream 320 can provide an efficient and/or cost-effective means of supplying hexene for operation of the polymerization reaction process. In an embodiment, at least a portion of the hexene of the heavy distillation side stream 320 can be employed in the polymerization reaction as, for example, a comonomer in the reaction. In an alternative embodiment, at least a portion of the heavy distillation side stream 320 can be routed to storage for subsequent use in a polymerization reaction or employed in any other suitable process. As will be appreciated by one of skill in the art, and with the help of this disclosure, at least a portion of the hexene can be recycled back to the reactor when the reactor is undergoing a polymerization reaction involving hexene as a comonomer. Further, as will be appreciated by one of skill in the art, and with the help of this disclosure, at least a portion of the hexene can be stored when the reactor is undergoing a polymerization reaction in the absence of hexene.

In some embodiments, at least a portion of the heavy distillation bottoms stream 310 and/or heavy distillation side stream 320 can be returned to the heavy distillation column 300. For example, at least a portion of the heavy distillation bottoms stream 310 and/or heavy distillation side stream 320 can be routed via a reboiler to the heavy distillation column 300 for additional processing.

In an embodiment, heavy distillation column 300 can be provided with one or more inlets and at least two outlets. The heavy distillation column 300 can be operated at a suitable temperature and pressure, for example as can be suitable to achieve separation of the components of the gas stream 210. For example, the heavy distillation column 300 can be operated at a temperature in a range of from about 15° C. to about 233° C., alternatively, from about 20° C. to about 200° C., alternatively, from about 20° C. to about 180° C., and/or a pressure in a range of from about 14.7 psi to about 527.9 psi, alternatively, from about 15.7 psi to about 348 psi, alternatively, from about 85 psi to about 290 psi. The heavy distillation column 300 can be configured and/or sized to provide for separation of a suitable volume of gases (e.g., a flash gas stream). As will be appreciated by one of skill in the art viewing this disclosure, the gas stream 210 can remain and/or reside within heavy distillation column 300 for any suitable amount of time, for example an amount of time as can be necessary to provide sufficient separation of the components within the heavy distillation column 300.

In an embodiment, the gas stream 210 can be introduced into the heavy distillation column 300 without a compressive step, that is, without compression of the gas stream 210 after it is emitted from the flash chamber 200 and before it is introduced into the heavy distillation column 300. In another embodiment, the gas stream 210 can be introduced into the heavy distillation column 300 at substantially the same pressure as the outlet pressure of flash chamber 200 (e.g., a pressure of from about 14.7 psia to about 527.9 psia, alternatively, from about 15.7 psia to about 348 psia, alternatively, from about 85 psia to about 290 psia at the outlet of the flash chamber 200). In still another embodiment, the gas stream 210 can be introduced into the heavy distillation column 300 without a significant compressive step. In an embodiment, gas stream 210 can be introduced into heavy distillation column 300 at a pressure in a range of from about 25 psi less than the pressure at which the gas stream 210 was emitted from the flash chamber 200 to about 25 psi greater than the pressure at which the gas stream 210 was emitted from the flash chamber 200, alternatively, from about 15 psi less than the pressure at which the gas stream 210 was emitted from the flash chamber 200 to about 15 psi greater than the pressure at which the gas stream 210 was emitted from the flash chamber 200, alternatively, from about 5 psi less than the pressure at which the gas stream 210 was emitted from the flash chamber 200 to about 5 psi greater than the pressure at which the gas stream 210 was emitted from the flash chamber 200. In an embodiment, the gas stream 210 can be introduced into the heavy distillation column 300 at a pressure in a range of from about 14.7 psia to about 527.8 psia, alternatively, from about 15.7 psia to about 348 psia, from about 85 psia to about 290 psia.

In an embodiment, the heavy distillation column 300 can be configured and/or operated such that each of the intermediate hydrocarbon stream 330, the heavy distillation bottoms stream 310, and an optional heavy distillation side stream 320 can comprise a desired portion, part, or subset of components of the gas stream 210. For example, as will be appreciated by one of skill in the art and with the help of this disclosure, the location of a particular stream outlet, the operating parameters of the heavy distillation column 300, the composition of the gas stream 210, or combinations thereof can be manipulated such that a given stream can comprise a particular one or more components of the gas stream 210.

In the embodiment of the PEP system 1000 shown in FIG. 1, the intermediate hydrocarbon stream 330 can be separated in the light distillation column 350 to form light hydrocarbon stream 380, light distillation bottoms stream 360, and optionally, light distillation side stream 370. At least one gaseous component can be emitted from the light distillation column 350 in light hydrocarbon stream 380, and the other gaseous components can be emitted from the light distillation column 350 in light distillation bottoms stream 360.

In an embodiment, light hydrocarbon stream 380 can be characterized as comprising ethylene. For example, ethylene can be present in light hydrocarbon stream 380 in an amount from about 50% to about 99% by total weight of the light hydrocarbon stream 380, alternatively from about 60% to about 98%, alternatively from about 70% to about 95%.

In an embodiment, the light hydrocarbon stream 380 can further comprise other light gases (e.g., ethane, methane, carbon dioxide, nitrogen, hydrogen, or combinations thereof). In some embodiments, the light hydrocarbon stream 380 can comprise ethylene and ethane.

In an embodiment, light distillation bottoms stream 360 can be characterized as comprising propane, butane, isobutane, pentane, hexane, heavier saturated hydrocarbons, or combinations thereof. In an embodiment, the light distillation bottoms stream 360 can be free of olefins, alternatively, substantially free of olefins, alternatively, essentially free of olefins, alternatively, consisting essentially of or consisting of non-olefins. For example, olefins can be present in light distillation bottoms stream 360 in an amount of less than about 1.0% by total weight of the light distillation bottoms stream 360, alternatively, less than about 0.5%, alternatively, less than about 0.1%. In an embodiment, the light distillation bottoms stream 360 can comprise olefin-free isobutane 365.

In an embodiment, light distillation side stream 370 can be characterized as comprising isobutane. In an embodiment, light distillation side stream 370 comprising, alternatively, consisting of or essentially consisting of, isobutane can be emitted from the light distillation column 350. The isobutane of light distillation bottoms stream 360 can comprise a different grade of isobutane than the isobutane of light distillation side stream 370. For example, light distillation bottoms stream 360 can comprise isobutane that is substantially free of olefins, and light distillation side stream 370 can comprise a recycle isobutane which can include olefins.

In an embodiment, at least a portion of the light distillation side stream 370 and/or light distillation bottoms stream 360 can be recycled. In some embodiments, recycling at least a portion of the light distillation side stream 370 and/or light distillation bottoms stream 360 can comprise routing, for example, via a suitable pump or compressor, at least a portion of the light distillation side stream 370 and/or light distillation bottoms stream 360 back to and/or introducing at least a portion of the light distillation side stream 370 and/or light distillation bottoms stream 360 into one or more components of the PEP system 1000, for example, into slurry loop reactor system 100 for reuse in a polymerization reaction. In an embodiment, at least a portion of the light distillation side stream 370 and/or light distillation bottoms stream 360 can be combined with various other components (catalysts, cocatalysts, etc.) to form a catalyst slurry that can be introduced into one or more of reactors 104, 106. Without wishing to be limited by theory, because at least a portion of light distillation bottoms stream 360 can be free of olefins and can comprise isobutane, the light distillation bottoms stream 360 can be mixed with catalytic components (e.g., catalysts, cocatalysts, etc.) without the risk of unintended polymerization reactions (e.g., polymerization prior to introduction into the one or more reactors). As such, at least a portion of light distillation bottoms stream 360 can serve as a source of olefin-free isobutane for a polymerization reaction. Recycling at least a portion of the light distillation side stream 370 and/or light distillation bottoms stream 360 can provide an efficient and/or cost-effective means of supplying isobutane for operation of the polymerization reaction process. In an alternative embodiment, at least a portion of the light distillation side stream 370 and/or light distillation bottoms stream 360 can be routed to storage for subsequent use in a polymerization reaction or employed in any other suitable process.

In some embodiments, at least a portion of the light distillation side stream 370 and/or light distillation bottoms stream 360 can be recycled to a TSA unit, for example via a sweeping gas stream. The light distillation bottoms stream 360 comprising olefin-free isobutane 365 can be recycled 366 to the TSA unit 500, for example via the sweeping gas stream 510, as shown in FIG. 1.

In other embodiments, at least a portion of the light distillation side stream 370 and/or light distillation bottoms stream 360 can be routed to storage for subsequent use in any suitable process.

In yet other embodiments, at least a portion of the light distillation side stream 370 and/or light distillation bottoms stream 360 can be returned to the light distillation column 350. For example, at least a portion of the light distillation side stream 370 and/or light distillation bottoms stream 360 can be routed via a reboiler to the light distillation column 350 for additional processing.

The light distillation column 350 can be configured and/or sized provide for separation of a suitable volume of gases. For example, the light distillation column 350 can be operated at a temperature in a range of from about 50° C. to about 20° C., alternatively, from about 40° C. to about 10° C., alternatively, from about 30° C. to about 5° C., and a pressure in a range of from about 14.7 psia to about 529.7 psia, alternatively, from about 15.7 psia to about 348 psia, alternatively, from about 85 psia to about 290 psia. The light distillation column 350 can be configured and/or sized to provide for separation of a suitable volume of intermediate hydrocarbon stream 330. As will be appreciated by one of skill in the art, the intermediate hydrocarbon stream 330 can remain and/or reside within light distillation column 350 for any suitable amount of time as can be necessary to provide sufficient separation of the components of intermediate hydrocarbon stream 330. In an embodiment, light distillation column 350 can be provided with at least two outlets.

In an embodiment, the light distillation column 350 can be configured and/or operated such that each of light hydrocarbon stream 380 and the light distillation bottoms stream 360 can comprise a desired portion, part, or subset of components of the intermediate hydrocarbon stream 330. For example, as will be appreciated by one of skill in the art with the aid of this disclosure, the location of a particular stream inlet or outlet, the operating parameters of the light distillation column 350, the composition of the intermediate hydrocarbon stream 330, or combinations thereof can be manipulated such that a given stream can comprise a particular one or more components of the intermediate hydrocarbon stream 330.

In an embodiment, the PEP process 2000 can generally comprise the step 2500 of purging the polymer stream to produce a purged polymer stream and a spent purge gas stream. In the embodiment of the PEP system 1000 shown in FIG. 1, a primary solids feed to the purge column 400 comprises typically the polymer stream 220. Generally, the polymer stream 220 comprises a solids discharge (e.g., polyolefin fluff, such as for example polyethylene fluff) that exits the flash chamber 200. A purpose of the purge column 400 is to remove residual hydrocarbon from polymer stream 220 and to provide a substantially-clean polymer fluff (e.g., polymer 425) with relatively small amounts of entrained volatile organic content. The polymer 425 (e.g., polymer fluff) can be transported or conveyed to an extrusion/loadout system for conversion to pellets and/or for distribution and sale as polyolefin pellet resin.

Referring to the embodiment of FIG. 1, the polymer stream 220 can comprise a polymer (e.g., polyethylene), unreacted monomer (e.g., ethylene, 1-hexene) and various gases (e.g., ethane, isobutane, hydrogen, methane, propane, butane, pentane, hexane, propylene). Processing (e.g., purging) the polymer stream 220 can yield the purged polymer stream 420 and the spent purge gas stream 430 generally comprising a purge gas (e.g., nitrogen), unreacted monomer (e.g., ethylene, 1-hexene), and various gases (e.g., ethane, isobutane, hydrogen, nitrogen, methane, propylene, propane, butane, pentane, hexane, heavier hydrocarbons).

Referring to the embodiment of FIG. 1, a purge gas 410 (e.g., an inert gas, nitrogen) can be circulated through purge column 400 to remove residual hydrocarbons via a spent purge gas stream 430. The spent purge gas stream 430 can be communicated to a separation unit, such as for example a TSA unit 500, for ethylene recovery.

In an embodiment, purge column 400 can be a cylindrical vessel having a relatively tall vertical section, a cover or head at the top, sloped sides or conical shape at the bottom with an opening for polymer fluff discharge. The polymer fluff to be degassed of volatile hydrocarbons can enter the vessel at the top, while the purge gas, typically nitrogen, can be introduced to the vessel in the sloped bottom sides. Flow can be countercurrent between the purge gas and polymer fluff in the vessel. In certain embodiments, a hydrocarbon rich purge gas (e.g., spent purge gas 430) can leave the purge column through an opening at the top, while a degassed fluff (e.g., purged polymer stream 420) can leave at the bottom of the purge column.

Degassing effectiveness in the purge column can be predicated on the maintenance of an uniform plug flow of the polymer fluff and purge gas in the purge column, thereby ensuring good contact between the two. A diameter (D) of the purge column can typically range from about 5 to about 6 feet, but a length (L) of the purge column can be chosen to achieve a residence time (e.g., from about 30 to about 180 minutes) sufficient for degassing the polymer fluff. In some embodiments, L/D ratios can range from about 4 to about 8; however, L/D ratios can be outside this range. In an embodiment, internal features can be employed in the purge column, such as a distributor plate for introducing purge gas (e.g., nitrogen), an inverted cone for facilitating plug flow of the polymer (e.g., to reduce bridging or channeling of the polymer fluff), and the like.

In one or more of the embodiments disclosed herein, processing the purged polymer stream 420 (e.g., polymer 425) comprises any suitable process or series of processes configured to produce a polymer product as can be suitable for commercial or industrial usage, storage, transportation, further processing, or combinations thereof.

In an embodiment, processing the purged polymer stream 420 can comprise routing the purged polymer stream 420 to a polymer processor. The polymer processor can be configured for the performance of a suitable processing means (e.g., to form various articles), nonlimiting examples of which include cooling, injection molding, melting, pelletizing, film blowing, cast film, blow molding, extrusion molding, rotational molding, thermoforming, cast molding, fiber spinning, and the like, or combinations thereof. Various additives and modifiers can be added to the polymer to provide better processing during manufacturing and for desired properties in the end product. Nonlimiting examples of such additives can include surface modifiers such as slip agents, antiblocks, tackifiers; antioxidants such as primary and secondary antioxidants; pigments; processing aids such as waxes/oils and fluoroelastomers; and/or special additives such as fire retardants, antistats, scavengers, absorbers, odor enhancers, and degradation agents.

The polymer can include other suitable additives. Such additives can be used singularly or in combination and can be included in the polymer before, during or after preparation of the polymer as described herein. Such additives can be added via known techniques, for example during an extrusion or compounding step such as during pelletization or subsequent processing into an end use article.

In an embodiment, the polymer processor can be configured to form a suitable polymer product. Nonlimiting examples of suitable polymer products as can result from processing the purged polymer stream include films, powders, pellets, resins, liquids, or any other suitable form as will be appreciated by those of skill in the art. Such a suitable output can be for use in, for example, one or more of various consumer or industrial products. For example, the polymer product can be utilized in any one or more of various articles, including, but not limited to, bottles, drums, toys, containers, household containers, utensils, film products, tanks, fuel tanks, pipes, membranes, geomembranes, and liners. In an embodiment, the polymer processor is configured to form pellets for transportation to a consumer product manufacturer.

In an embodiment, the PEP process 2000 can generally comprise the step 2600 of contacting the spent purge gas stream with a temperature swing adsorber contactor (TSAC) to yield a loaded TSAC and a non-adsorbed gas stream. In an embodiment, at least one gaseous component (e.g., ethylene) can be separated from the spent purge gas stream 430 during step 2600.

In one or more one or more of the embodiments disclosed herein, separating at least one gaseous component from a gas stream (e.g., the spent purge gas stream 430) generally comprises any suitable method of selectively separating at least a first chemical component or compound from a stream comprising the first chemical component or compound and one or more other chemical components, compounds, or the like. In various embodiments, the gaseous component separated from the gas stream can comprise one or more hydrocarbons. Nonlimiting examples of such hydrocarbons include alkanes (e.g., ethane, butane, isobutane, hexane, and the like, or combinations thereof) and alkenes or olefin monomers (e.g., ethylene) or optional comonomers. In an embodiment, the gaseous component separated from the gas stream can comprise an unreacted hydrocarbon monomer, e.g., ethylene. Optionally, the gaseous component separated from the gas stream can comprise an unreacted hydrocarbon comonomer. In an embodiment, the gaseous component separated from the gas stream can comprise an unreacted hydrocarbon monomer (e.g., ethylene, alone or in combination with other hydrocarbons, such as, ethane, isobutane, hexane, or combinations thereof), or optionally, hydrocarbon comonomer alone or in combination with other hydrocarbons, such as, isobutane, hexane, or combinations thereof. In an embodiment, the gaseous component separated from the gas stream can comprise ethylene, alone or in combination with isobutane. In an embodiment, capturing isobutane can result in a savings of the cost of the captured isobutane and reduce the presence of isobutane in flare emissions. Nonlimiting examples of suitable separating means include distilling, vaporizing, flashing, filtering, membrane screening, absorbing, adsorbing, molecular weight exclusion, size exclusion, polarity-based separation, or combinations thereof.

In an embodiment, at least one gaseous component (e.g., ethylene) can be separated from the spent purge gas stream 430 by temperature swing adsorption. Recovering ethylene from the spent purge gas stream 430 can generally comprise contacting the spent purge gas stream 430 with the TSAC in a TSA unit 500 to yield a loaded TSAC generally comprising TSAC-adsorbed ethylene, and a non-adsorbed gas stream 520 generally comprising nitrogen, ethane, isobutane.

For purposes of the disclosure herein, the term "loaded" when used to describe or when referring to a TSAC (e.g., "loaded TSAC"), is intended to be nonlimiting, and is intended to denote (e.g., mean, signify, indicate, represent, etc.) that the TSAC has an amount of a hydrocarbon (e.g., ethylene, ethane, etc.) adsorbed therein (e.g., adsorbed ethylene, adsorbed ethane, etc.). Further, for purposes of the disclosure herein, the term "loaded" when used to describe a TSAC (e.g., "loaded TSAC"), is intended to include any amount of an adsorbed hydrocarbon, such as for example an amount of adsorbed hydrocarbon of equal to or greater than about 10%, alternatively equal to or greater than about 15%, alternatively equal to or greater than about 20%, alternatively equal to or greater than about 25%, alternatively equal to or greater than about 30%, alternatively equal to or greater than about 40%, alternatively equal to or greater than about 50%, alternatively equal to or greater than about 60%, alternatively equal to or greater than about 70%, alternatively equal to or greater than about 80%, alternatively equal to or greater than about 90%, alternatively equal to about 100%, based on the adsorption capacity of the TSAC at a given temperature (e.g., first temperature). Without wishing to be limited by theory, the adsorption capacity of the TSAC at a given temperature (e.g., first temperature) can be defined as the ratio of the maximum amount of hydrocarbon that can be adsorbed by the TSAC to the amount of hydrocarbon adsorber present in the TSAC, and it can be expressed in g adsorbed hydrocarbon/g hydrocarbon adsorber. As will be appreciated by one of skill in the art and with the help of this disclosure, the term "adsorbed hydrocarbon" refers to a hydrocarbon (e.g., ethylene, ethane, etc.) that is adsorbed or associated with an adsorbent (e.g., adsorbent associated hydrocarbon) in a reversible fashion, wherein the adsorbent is a hydrocarbon adsorber of the type disclosed herein.

In an embodiment, the loaded TSAC can be a partially loaded TSAC, wherein the partially loaded TSAC can comprise an amount of adsorbed hydrocarbon of from about 10% to about 50%, alternatively from about 15% to about 45%, or alternatively from about 20% to about 40%, based on the adsorption capacity of the TSAC at the first temperature.

In an embodiment, the loaded TSAC can be a substantially loaded TSAC, wherein the substantially loaded TSAC can comprise an amount of adsorbed hydrocarbon of from about 50% to about 99%, alternatively from about 55% to about 95%, or alternatively from about 60% to about 90%, based on the adsorption capacity of the TSAC at the first temperature.

In an embodiment, the loaded TSAC can be a completely or fully loaded TSAC (alternatively referred to as a saturated TSAC), wherein the completely loaded TSAC can comprise an amount of adsorbed hydrocarbon of about 100%, alternatively about 99.5%, or alternatively about 99%, based on the adsorption capacity of the TSAC at the first temperature.

As will be appreciated by one of skill in the art, and with the help of this disclosure, the TSAC can undergo an adsorption step (e.g., the TSAC can adsorb) to yield a loaded TSAC, such as for example a substantially loaded TSAC or a completely loaded TSAC, and subsequently the loaded TSAC (e.g., substantially loaded TSAC, completely loaded TSAC) can undergo a regeneration step (e.g., the TSAC can regenerate) to yield a TSAC or a partially loaded TSAC. The TSAC can be characterized by a first adsorption capacity at the first temperature, and by a second adsorption capacity at a second temperature, wherein the first temperature is greater than the second temperature, and wherein the first adsorption capacity is greater than the second adsorption capacity, thereby enabling an adsorption step at the first temperature and a desorption/regeneration step at the second temperature.

In an embodiment, separating at least one gaseous component from the spent purge gas stream can comprise contacting the spent purge gas stream with an adsorbent (e.g., TSAC, as disclosed herein), for example, so as to allow the gaseous component to be adsorbed by the adsorbent. In such an embodiment, separating at least one gaseous component from the spent purge gas stream comprises selectively adsorbing the at least one gaseous component from a spent purge gas stream. In such an embodiment, adsorbing the at least one gaseous component from the spent purge gas stream generally comprises contacting the spent purge gas stream with a suitable adsorbent, allowing the at least one component to be adsorbed by the adsorbent, and, optionally, removing a waste stream comprising unadsorbed gases (e.g., non-adsorbed gas stream 520). In an additional embodiment, separating at least one gaseous component from the spent purge gas stream can further comprise liberating the adsorbed gaseous component from the adsorbent (e.g., recovered adsorbed gas stream 530).

In an embodiment, the TSAC comprises a plurality of hollow tubes and a hydrocarbon adsorber, wherein the hollow tube comprises a hollow tube outer surface, wherein at least a portion of the hollow tube outer surface is in contact with the hydrocarbon adsorber. In an embodiment, a physical structure of the TSAC can be arranged to provide for a sufficient contact surface area between the hydrocarbon adsorber and the hollow tube outer surface, which in turn can provide for rapid heat exchange, thereby enabling rapid cycles of a temperature swing adsorption process, as will be described in more detail later herein.

In an embodiment, the hollow tubes comprise very small diameter tubes (e.g., microtubes). In an embodiment, the hollow tubes can be characterized by an inner diameter of from about 0.1 mm to about 5 mm, alternatively from about 0.2 mm to about 2 mm, or alternatively from about 0.25 mm to about 1.5 mm. As will be appreciated by one of skill in the art and with the help of this disclosure, a cross-section of the hollow tubes has a circular geometry; however, other geometries of the cross-section of the hollow tubes can be possible, such as for example oval, square, hexagonal, etc.

In an embodiment, a heating transfer fluid (e.g., a cooling fluid, a heating fluid) can pass through at least a portion of the hollow tube (e.g., through at least a portion of an inner hollow part of the tubes).

In an embodiment, the hollow tubes can be characterized by a hollow tube thickness of from about 0.1 mm to about 1 mm, alternatively from about 0.15 mm to about 0.8 mm, or alternatively from about 0.2 mm to about 0.5 mm. Generally, a tube thickness can be calculated by subtracting an inner tube diameter from an outer tube diameter and dividing such difference by 2.

In an embodiment, the hollow tubes can be characterized by a hollow tube length. The hollow tube length can vary depending on the overall desired length of the TSAC. In some embodiments, the hollow tubes, which can carry cooling and/or heating fluid, can be aligned substantially parallel to the flow of a feed gas (e.g., spent purge gas 430, sweeping gas 510, etc.). In other embodiments, the hollow tubes can be aligned substantially perpendicular, or at any other suitable angle, to the direction of flow of feed gas. In yet other embodiments, the hollow tubes can be changing direction throughout a length of the TSAC, such as for example in a net-like structure, mesh structure, weaved structure, braided structure, etc.

In an embodiment, the hollow tubes can be characterized by a hollow tube length of from about 1 mm to about 500 mm, alternatively from about 10 mm to about 250 mm, or alternatively from about 50 mm to about 150 mm. In an embodiment, the hollow tubes can be characterized by any suitable hollow tube length. As will be appreciated by one of skill in the art, and with the help of this disclosure, the hollow tube length can be any suitable length that can enable the rapid cycles of a temperature swing adsorption process, as will be described in more detail later herein.

The hollow tubes can be manufactured from any suitable material so long as their integrity is capable of withstanding the gaseous environments as well as pressure and temperature swings which they will be subjected to when used in a TSA process.

In an embodiment, the hollow tubes comprise a thermally conductive material. As will be appreciated by one of skill in the art, and with the help of this disclosure, during a TSA process, the hollow tubes have to be capable of effectively transmitting heat (e.g., a thermal wave) between an inner hollow tube surface and an outer hollow tube surface.

In an embodiment, the hollow tubes can comprise a metal, aluminum, nickel, an alloy, stainless steel, thermally conductive polymers, polymeric materials, latexes, polyvinylidene chloride latex, carbon, glass, ceramics, or combinations thereof.

In an embodiment, the TSAC comprises a hydrocarbon adsorber. In an embodiment, the hydrocarbon adsorber comprises a substance, material and/or compound capable of facilitating adsorption and desorption of a hydrocarbon (e.g., ethylene, ethane, etc.) from a hydrocarbon mixture (e.g., spent purge gas stream) by way of a temperature swing adsorption process. For example, the hydrocarbon adsorber can comprise a substance, material and/or compound capable of adsorbing hydrocarbons, preferably in a selective manner. Generally, the hydrocarbon adsorber can comprises any material capable of selectively adsorbing one or more hydrocarbon components of a gas mixture (e.g., a spent purge gas stream). In an embodiment, the hydrocarbon adsorber can selectively adsorb one or more hydrocarbons at a first temperature, and can selectively desorb (e.g., regenerate) one or more hydrocarbons at a second temperature, wherein the first temperature is greater than the second temperature.

Nonlimiting examples of hydrocarbon adsorbers suitable for use in the present disclosure include a molecular sieve, a 4 A molecular sieve, a zeolite, metal-organic frameworks (MOFs), carbon, molecular sieve carbon, zeolitic imidazolate frameworks (ZIFs), or combinations thereof.

In an embodiment, the hydrocarbon adsorber comprises a zeolite. The term "zeolite" generally refers to a particular group of hydrated, crystalline metal aluminosilicates. Zeolites typically are ordered porous crystalline aluminosilicates having a structure with pores/cavities and channels interconnected by channels. The pores and channels throughout the crystalline material generally can be of a size to allow selective separation of hydrocarbons. Generally, zeolites exhibit a network of $SiO_4$ and $AlO_4$ tetrahedra in which aluminum and silicon atoms are crosslinked in a three-dimensional framework by sharing oxygen atoms. In the framework, the ratio of oxygen atoms to the total of aluminum and silicon atoms can be equal to 2. The framework exhibits a negative electrovalence that typically is balanced by the inclusion of cations within a crystal structure of the aluminosilicates, such as for example metals, alkali metals, alkaline earth metals, or hydrogen.

Nonlimiting examples of zeolites suitable for use as hydrocarbon adsorbers in the present disclosure include a cationic zeolite, an aluminosilicate, an alkali metal aluminosilicate, a sodium aluminosilicate, an X zeolite, a NaX zeolite, a 13X zeolite, an A zeolite, a NaA zeolite, KA zeolite, NaCaA zeolite, or combinations thereof.

In an embodiment, the hydrocarbon adsorber comprises a porous material. Such porous material can comprise open pores that are interconnected to allow hydrocarbons to enter the hydrocarbon adsorber and be adsorbed in such pores. In some embodiments, the size of the pores can be such that only certain hydrocarbons will be able to enter the pores and be adsorbed within the pores. In an embodiment, the pores of the hydrocarbon adsorber can have a size of from about 2 Angstroms to about 10 Angstroms, alternatively from about 2 Angstroms to about 6 Angstroms, alternatively from about 3 Angstroms to about 5 Angstroms, or alternatively about 4 Angstroms.

In some embodiments, a size of the pores within the zeolite is about 4 Angstroms, thereby rendering such zeolite (also known as a 4 Å molecular sieve or a 4 A zeolite) suitable for selectively separating certain hydrocarbons, such as for example separating ethylene from ethane.

In an embodiment, the TSAC further comprises a support, wherein the hydrocarbon adsorber contacts at least a portion of the support, is distributed throughout the support, or combinations thereof, and whereby the hydrocarbon adsorber is structurally supported by the support. In an embodiment, the hydrocarbon adsorber can be disposed about the support. In an embodiment, the hydrocarbon adsorber can be associated with the support.

The support can be comprised of any suitable material and/or of any suitable construction and can be porous or non-porous. In some embodiments, the support can be comprised entirely of a hydrocarbon adsorber. In other embodiments, the support can be comprised entirely of a (relatively) non-adsorbent material towards hydrocarbons.

In an embodiment, the support can contact a hydrocarbon adsorber, wherein the hydrocarbon adsorber comprises a layer on the support; wherein the hydrocarbon adsorber can be embedded within the structure of the support, or the like, or combinations thereof.

In an embodiment, the support comprises a film, a foil, a mesh, a fiber cloth, a woven fiber mesh, a woven wire mesh, a metallic woven wire mesh, a polymeric membrane, a surface treated material, a surface treated metal foil, a woven fiber cloth, or combinations thereof.

In an embodiment, the support comprises a thermally conductive polymer (e.g., a porous thermally conductive polymer, a foamed thermally conductive polymer, etc.). As will be appreciated by one of skill in the art, and with the help of this disclosure, during a TSA process, the TSACs have to be capable of effectively transmitting heat (e.g., a thermal wave) across the TSAC. Further, as will be appreciated by one of skill in the art, and with the help of this disclosure, when the support is a porous thermally conductive polymer and/or a foamed thermally conductive polymer, the hydrocarbon adsorber can be present in the pores of such porous and/or foamed support material, whereby the hydrocarbon adsorber is structurally supported by the support.

Nonlimiting examples of supports suitable for use in the present disclosure include cellulose acetate, polyvinylpyrrolidone, or combinations thereof.

In some embodiments, the support can be a woven fiber cloth or fiber mesh wherein at least a fraction of fibers are comprised of a hydrocarbon adsorber and wherein the remaining fraction is comprised of a non-adsorbent material. In some embodiments, the hydrocarbon adsorber can also be comprised of zeolite crystals embedded within the support.

In an embodiment, the thickness of a support layer can be any effective thickness. For purposes of the disclosure herein the effective thickness of a support layer represents any thickness capable of providing at least a minimum integrity needed under TSA process conditions for an intended overall structure of the TSAC, whether it is a spiral wound structure, a layered non-spiral structure, etc.

In an embodiment, the support comprises a non-adsorbent material towards hydrocarbons. In such embodiment, the support can be treated by any suitable treating technique to incorporate at least an effective amount of a hydrocarbon adsorber on/within the support material. Nonlimiting examples of treating techniques for applying a hydrocarbon adsorber to the support suitable for use in the present disclosure include wash coating techniques, in situ crystallization methods that deposit a hydrocarbon adsorber directly onto the support from a synthesis solution, doctor-blading, spraying, spray-coating, electrodeposition, dry-wet spinning, or the like.

In an embodiment, the support can be coated with a hydrocarbon adsorber by wash-coating. A typical wash-coating process involves a slurry preparation (e.g., molecular sieve particles, a suitable binder, and optionally a viscosifying agent), slurry application by washing or dipping, drying, and/or sintering. Once a wet coating is formed, such coating has to be dried and sintered at relatively high temperatures (e.g., from about 300° C. to about 600° C.) to establish binding among coating components and adhesion between coating and a surface of the support.

In an embodiment, the support comprises a porous material (e.g., a foamed material) and the hydrocarbon adsorber can be applied in a manner in which particles of hydrocarbon adsorber fill at least a portion of the pores of a porous structure of the support. For example, a slurry containing hydrocarbon adsorber crystals can be soaked into, or pressured through, a porous layered support material, then such layered support can be dried and/or calcined.

As will be appreciated by one of skill in the art and with the help of this disclosure, a coated support can typically have two major opposing support surfaces, and one or both of these surfaces can be coated with the hydrocarbon adsorber. In an embodiment, a thickness of the support, plus applied hydrocarbon adsorber and/or any other materials (e.g., a desiccant, a catalyst, etc.) can range from about 0.010 mm to about 2 mm, alternatively from about 0.10 mm to about 1 mm, or alternatively from about 0.15 mm to about 0.3 mm.

In an embodiment, the TSAC can be assembled by using any suitable methodology compatible with materials and methods disclosed herein. In some embodiments, the hollow tubes and the support (e.g., a foil type support, a layered support, etc.) can be in good thermal contact with each other. In such embodiments, the hollow tubes and the support can be brazed, welded, or soldered together in at least some locations to both increase heat transfer rates and strengthen the structure.

In an embodiment, the TSAC comprises a TSAC structure wherein a plurality of hollow tubes contacting a hydrocarbon adsorber can be housed, and wherein a geometry of the TSAC structure is defined by the support. In such embodiment, the TSAC structure can have a cylindrical geometry.

In some embodiments, the hollow tubes can extend past the hydrocarbon adsorber, and the ends of the hollow tubes can be sealed away from the hydrocarbon adsorber (e.g., in a sealing end cap), such that a heat exchange fluid that passes through the hollow tubes does not contact the hydrocarbon adsorber. Nonlimiting examples of materials suitable for use in the sealing end caps include solder, brazing material, and/or polymeric materials such as epoxy. As will be appreciated by one of skill in the art, and with the help of this disclosure, the sealing end cap should be of suitable physical integrity to be able to withstand prolonged use at operating conditions.

In an embodiment, the TSAC can comprise a gas mixture inlet and a gas mixture outlet. In some embodiments, open flow channels can be provided through the hydrocarbon adsorber for the flow of gaseous mixtures (e.g., a spent purge gas, a sweeping gas, etc.), wherein the open flow channels can be continuous between the gas mixture inlet and the gas mixture outlet of the TSAC. In some embodiments, the gas mixture inlet and the gas mixture outlet can be located on a body of the TSAC between the sealing end caps. As will be appreciated by one of skill in the art, and with the help of this disclosure, the heat exchange fluid that passes through the hollow tubes should generally be kept isolated from a feed gas mixture and product gases flowing to, through, and from the open flow channels. This can be accomplished by any suitable means, such as by having a suitable sealing device (e.g., sealing end cap) at each end of the TSAC.

In some embodiments, the open flow channels and hollow tubes can be oriented substantially parallel to each other in the TSAC. Inlet and outlet ends of each of the open flow channels and the hollow tubes can be oriented in the TSAC on substantially opposite ends, such that feed gases and heat exchange fluids pass substantially parallel to one another from one end of the TSAC to the other. In other embodiments, the open flow channels and hollow tubes can be oriented substantially non-parallel to each other in the TSAC.

In an embodiment, a TSAC structure can comprise spacers. Generally, spacers can provide a fixed distance between layers or sheets of a structure (e.g., a TSAC structure). The spacers can be either integral to the TSAC of they can be a non-integral independent material. When spacers are integral to the TSAC (e.g., support), then the spacers could be formed during manufacturing of the TSAC, such as dimples or corrugations (e.g., within the support) of a predetermined size to provide a desired flow channel volume of the open flow channels. When spacers are not integral to the TSAC, then the spacers can be comprised of any suitable material that can be relatively inactive in the TSAC and that should not typically decompose under TSA process conditions. Nonlimiting examples of spacer materials suitable for use in the present disclosure include particles, such as glass microspheres, wires of suitable size, and the like, or combinations thereof.

In an embodiment, a layer of hydrocarbon adsorber can be applied to a sheet of support, as previously described herein, before placement of the hollow tubes and/or after placement of the hollow tubes in contact with the hydrocarbon adsorber and/or the support.

In some embodiments, the TSAC can comprise a spiral wound structure, wherein the hollow tubes can be supported by at least one layer of the hydrocarbon adsorber and, in most cases, can be sandwiched between two surfaces of hydrocarbon adsorber. A spiral wound structure of a TSAC can be constructed by a prefabrication technique wherein a plurality of hollow tubes can be placed on a substantially flat sheet of hydrocarbon adsorber. In an embodiment, a spiral wound structure can be assembled by wounding structure components around a mandrel of suitable composition and dimensions relative to a desired final spiral wound structure of the TSAC. In an embodiment, a suitable banding device (e.g., bands, fasteners, clasps, ties, clips, pins, etc.) can be used to secure the spiral wound structure in a desired geometry (e.g., cylindrical), and to prevent it from unraveling/telescoping. Brazing material or adhesives can optionally be used to bond the hollow tubes to the hydrocarbon adsorber, thereby adding rigidity and strength to the overall structure.

In other embodiments, the TSAC can comprise a stacked layered sheet structure. The stacked layered sheet structure can be assembled by first preparing a single layer substructure, then folding it back and forth on itself multiple times until a final desired stacked layered sheet structure can be achieved.

In yet other embodiments, the TSAC can comprise a plurality of hollow tubes in contact with an inner surface of a support layer, wherein an outer surface of the same support layer can be in contact with the hydrocarbon adsorber. The TSAC can comprise a plurality of support layers. In such embodiments, the TSAC can further comprise spacers, wherein the spacers can define open flow channels. A distance between the support layers can be defined by the outer diameter of the hollow tubes.

In still yet other embodiments, the TSAC can comprise a support in a corrugated form, wherein the support comprises folds or furrows. In such embodiments, the hollow tubes can occupy at least a portion of the folds. Both sides of the corrugated support can comprise the hydrocarbon adsorber, except for surfaces within the folds, which can be occupied by the hollow tubes. Open flow channels can be formed between two opposing corrugated support layers.

In still yet other embodiments, the TSAC can comprise a support, wherein an inner surface of the support contacts the hollow tubes and can be coated with the hydrocarbon adsorber, and wherein an outer surface of the support is not coated with the hydrocarbon adsorber. In such embodiments, the inner surface of the support can be coated with the hydrocarbon adsorber before and/or after contacting the inner surface of the support with the hollow tubes. In some embodiments, an outer surface of the hollow tubes can be coated with the hydrocarbon adsorber. The support layers contacting the hollow tubes and the hydrocarbon adsorbers can be stacked in any suitable manner to form the TSAC. For example, the outer surfaces of the support from two adjacent layers can contact each other, and the inner surfaces comprising the hollow tubes can contact each other, wherein the spacing between the hollow tubes can create open flow channels. As another example, the outer surface of the support from one layer can contact the inner surface of a support comprising the hollow tubes from an adjacent layer, wherein the spacing between the hollow tubes can create open flow channels. Such configurations can alternate within a TSAC. The TSAC can further comprise spacers to control the position and size of open flow channels. Other configurations of TSACs are described in more detail in U.S. Patent Publication No. 20120222554 A1, which is incorporated by reference herein in its entirety.

In an embodiment, the TSAC comprises a plurality of hollow fiber contactors. In an embodiment, the hollow fiber contactor comprises the support in contact with the outer surface of the hollow tubes, wherein the hollow fiber contactor has an outer cylindrical geometry owing to a cylindrical geometry of the support. In some embodiments, the hollow fiber contactors can be bundled together, thereby creating open flow spaces between adjacent hollow fiber contactors.

Figure 4A:
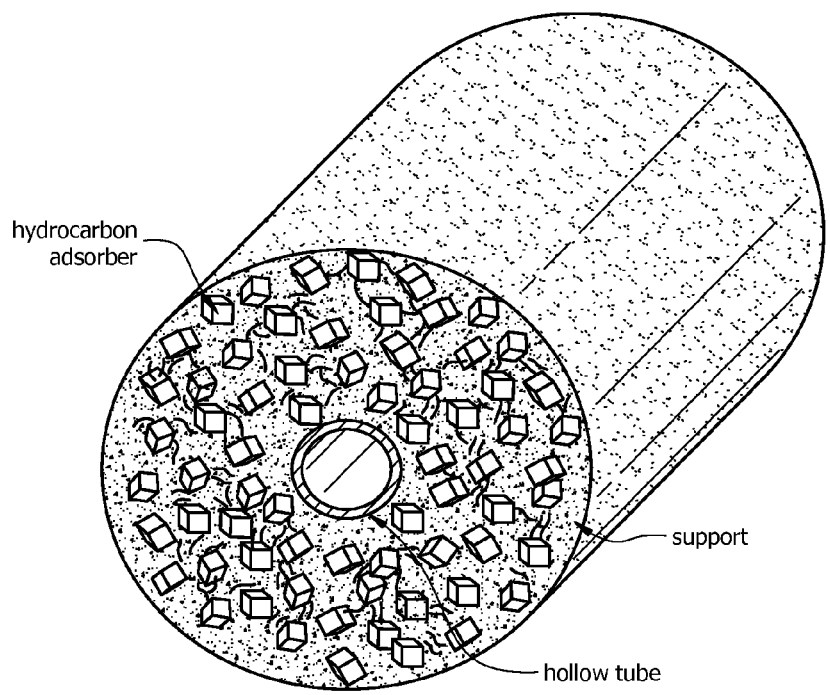
FIG. 4A illustrates a schematic of an isometric view of a hollow fiber contactor.
Figure 4B:
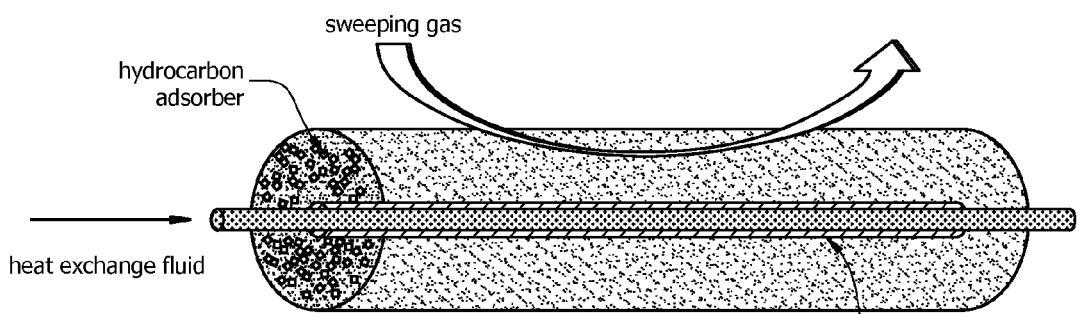
FIG. 4B illustrates a schematic of a side view of a hollow fiber contactor.

In an embodiment, the hollow fiber contactor comprises a hollow tube, and a hydrocarbon adsorber dispersed throughout and supported within a support (e.g., porous polymer) as shown in FIG. 4A. In an embodiment, a heat exchange fluid can pass through the hollow tube, while a sweeping gas can flow across the support/hydrocarbon adsorber, as shown in FIG. 4B.

In an embodiment, hollow fiber contactors can be assembled by using a nonsolvent phase inversion technique commonly referred to as "dry-wet spinning." In such embodiment, polymer solutions (e.g., polymer support solutions) comprising hydrocarbon adsorber particles (e.g., zeolite particles, molecular sieve particles, etc.), solvents, nonsolvents, additives for tuning phase equilibria, can be extruded through a die into a nonsolvent quench bath, thereby forming a hollow fiber. In an embodiment, the hollow fiber comprises a continuous polymer network wherein hydrocarbon adsorber particles are entrapped within such polymer network. In an embodiment, the polymer solution comprises N-methyl-2-pyrrolidone (NMP), cellulose acetate, and polyvinylpyrrolidone, wherein polyvinylpyrrolidone can act as a pore former. In an embodiment, the hydrocarbon adsorber comprises a 4 Å molecular sieve. In an embodiment, the hollow tube of the hollow fiber contactor can be formed by coating an inner surface of the hollow fibers with a polymer, such as for example a latex form of polyvinylidene chloride. Hollow fiber contactors, which can also be referred to as hollow fiber adsorbents, are described in more detail in Ind. Eng. Chem. Res. 2009, 48, pp 7314-7324, which is incorporated by reference herein in its entirety.

TSACs rely on temperature swing adsorption (TSA) as a process for selectively separating at least one gaseous component from a gas mixture (e.g., hydrocarbon mixture, spent purge gas stream, etc.). TSA processes rely on the fact that under pressure gases tend to be adsorbed within a pore structure of a microporous adsorbent material (e.g., hydrocarbon adsorber) or within a free volume of a polymeric material. Without wishing to be limited by theory, gas adsorption within an adsorption bed is generally an exothermic process, thereby causing a rise in temperature during such adsorption. An elevated temperature can cause the gas to be desorbed, which is generally undesirable during an adsorption step. One way to circumvent this problem is by cooling the adsorption bed during the adsorption step. By cyclically swinging the temperature of adsorbent beds, TSA processes can be used to separate gases in a mixture when used with an adsorbent that is selective for one or more of the components of a gas mixture.

In an embodiment, a TSAC can be repeatedly cycled through at least two steps: an adsorption step and a regeneration/desorption step (e.g., thermally assisted desorption step). Regeneration of the TSACs can be achieved by increasing the temperature of the TSAC to a temperature effective in desorbing at least a portion of the gas or gases that were adsorbed by the TSAC during the adsorption step. The TSAC can then be cooled so that another adsorption step can be performed. In some embodiments, the regeneration step can be assisted with use of a partial pressure purge displacement, or even a pressure swing, such as for example running a sweeping gas which can be pressurized across a TSAC. For purposes of the disclosure herein, any combination of processes that involves a thermally assisted desorption step, whether it is used in conjunction with a pressure change or not, will be referred to as TSA or TSA process.

In an embodiment, the TSA process can be conducted with rapid cycles, in which case it can be referred to as a rapid cycle temperature swing adsorption (RCTSA) process. For purposes of the disclosure herein, the terms TSA and RCTSA can be used interchangeably.

In an embodiment, the TSAC can be characterized by a cycle time of from about 10 seconds to about 1 hour, alternatively from about 15 seconds to about 30 minutes, or alternatively from about 30 seconds to about 10 minutes. For purposes of the disclosure herein, the cycle time of the TSAC can be defined as the time between the start of two successive adsorption steps, e.g., a time frame necessary to complete an adsorption step and a regeneration step that are consecutive.

In an embodiment, the relatively small dimensions of the hollow tubes and of the TSACs can effectively utilize/maximize surface area for heat exchange while reducing/minimizing the mass and/or total sensible heating requirements of the TSAC. In an embodiment, the TSAC can be characterized by a relatively low mass per surface area, given the porosity of the hydrocarbon adsorber and the relatively small dimensions of the hollow tubes. Generally, the TSAC is characterized by relatively short heat transfer distances, wherein a heat transfer can occur between a heat exchange fluid and the hydrocarbon adsorber and/or support, thereby enabling relatively rapid temperature swings (e.g., RCTSA) when used for thermal swing adsorption. The TSAC can provide a system for generation of relatively sharp thermal waves in both the hydrocarbon adsorber and/or support, as well as in the hollow tubes (e.g., heat transfer fluid channels). In some embodiments, such sharp thermal waves can enable both selective sequential desorption of multiple adsorbed species (e.g., different hydrocarbons) and enable efficient heat recovery.

In an embodiment, during the adsorption step, a cooling fluid can pass through (e.g., be flowed through) at least a portion of the hollow tubes prior to and/or during contacting the TSAC with a gaseous mixture (e.g., spent purge gas stream). Nonlimiting examples of cooling fluids suitable for use in the present disclosure include water, tap water, process water, an aqueous solution, or combinations thereof. The presence of the cooling fluid in the hollow tubes can advantageously increase the total heat capacity of the TSAC to limit a temperature rise during the adsorption step to an effectively small range.

In an embodiment, during the regeneration step, a heating fluid can pass through (e.g., be flowed through) at least a portion of the hollow tubes during heating the loaded TSAC. Nonlimiting examples of heating fluids suitable for use in the present disclosure include warm water, hot water, steam, or combinations thereof.

In some embodiments, the heat exchange fluid (e.g., cooling fluid, heating fluid) can be recovered subsequent to passing through at least a portion of the hollow tubes, to yield a recovered heat exchange fluid. As will be appreciated by one of skill in the art, and with the help of this disclosure, a temperature of the recovered heat exchange fluid could need to be adjusted (e.g., cool the cooling fluid, heat the heating fluid, etc.) prior to reusing the recovered heat exchange fluid in a TSAC.

In an embodiment, the adsorption step can occur at a first temperature and the regeneration step can occur at a second temperature. For purposes of the disclosure herein, the first temperature of the adsorption step is considered to be about the same temperature as the temperature of the cooling fluid, and about the same as the temperature of the TSAC during the adsorption step, given the efficient heat transfer that occurs within the TSAC. Further, for purposes of the disclosure herein, the second temperature of the regeneration step is considered to be about the same temperature as the temperature of the heating fluid, and about the same as the temperature of the TSAC during the regeneration step (e.g., loaded TSAC), given the efficient heat transfer that occurs within the TSAC. As will be appreciated by one of skill in the art, and with the help of this disclosure, this efficient heat transfer is what enables the short cycle times (e.g., RCTSA) as previously described herein. Further, as will be appreciated by one of skill in the art, and with the help of this disclosure, a fluid velocity of the heat exchange fluid within the hollow tubes can be adjusted such that the heat exchange fluid does not substantially change its temperature while passing through the hollow tubes. In an embodiment, the heat exchange fluid can be characterized by an initial temperature (e.g., a temperature at an entrance point into a hollow tube) and a final temperature (e.g., a temperature at an exit point from a hollow tube). In some embodiments, a difference between an initial temperature and a final temperature, wherein the smaller value is subtracted from the larger value, can be less than about 10° C., alternatively less than about 9° C., alternatively less than about 8° C., alternatively less than about 7° C., alternatively less than about 6° C., alternatively less than about 5° C., alternatively less than about 4° C., alternatively less than about 3° C., alternatively less than about 2° C., or alternatively less than about 1° C.

In an embodiment, the first temperature can be in the range of from about 10° C. to about 100° C., alternatively from about 25° C. to about 75° C., or alternatively from about 30° C. to about 60° C.

In an embodiment, the second temperature can be in the range of from about 20° C. to about 200° C., alternatively from about 40° C. to about 150° C., or alternatively from about 50° C. to about 100° C.

In an embodiment, the second temperature can be greater than the first temperature by equal to or greater than about 10° C., alternatively by greater than about 25° C., or alternatively by greater than about 50° C.

In an embodiment, the use of very small inner diameter hollow tubes to contain the heat exchange fluid, in conjunction with relatively high crush and burst strength capabilities of the hollow tubes and hydrocarbon adsorber and/or support, can enable using of the TSAC with relatively high differential pressures between a feed fluid (e.g., gas mixture, spent purge gas, sweeping gas, etc.) and the heat exchange fluid. In some embodiments, such relatively high differential pressures can be at least about 100 psi, alternatively at least about 200 psi, alternatively at least about 300 psi, alternatively at least about 400 psi, alternatively at least about 500 psi, alternatively from about 100 psi to about 2,000 psi, alternatively from about 300 psi to about 1,500 psi, alternatively from about 400 psi to about 1,000 psi, alternatively from about 500 psi to about 750 psi, or alternatively from about 100 psi to about 200 psi.

In an embodiment, the spent purge gas stream can be contacted with a TSAC to yield a loaded TSAC and a non-adsorbed gas stream during an adsorption step. In such embodiment, the adsorption step can occur at a first temperature. In an embodiment, the spent purge gas stream can be characterized by a pressure of from about 100 kPa to about 200 kPa, alternatively from about 120 kPa to about 180 kPa, or alternatively 140 kPa to about 160 kPa.

Referring to the embodiment of FIG. 1, the spent purge gas stream 430 that is emitted from purge column 400 can have a temperature that is higher than the first temperature. In such embodiment, the spent purge gas stream can be optionally cooled to about the first temperature prior to contacting at least a portion of the spent purge gas stream with the TSAC. For example, the spent purge gas stream can be sent to a heat exchanger for cooling prior to contacting with the TSAC.

In an embodiment, the TSAC can be cooled and/or maintained to about the first temperature during the adsorption step by passing a cooling fluid through at least a portion of the hollow tubes of the TSAC.

In an embodiment, the spent purge gas stream can comprise a low concentration of ethylene, e.g., the spent purge gas stream comprises a dilute ethylene stream. In an embodiment, the ethylene of the spent purge gas stream can be characterized by a partial pressure of from about 1 kPa to about 20 kPa, alternatively from about 2 kPa to about 15 kPa, or alternatively 8 kPa to about 12 kPa. In an embodiment, at least a portion of the ethylene present in the spent purge gas stream can be adsorbed by the TSAC at the first temperature to yield TSAC-adsorbed ethylene. In an embodiment, the loaded TSAC comprises TSAC-adsorbed ethylene.

In an embodiment, the spent purge gas stream can comprise a low concentration of ethane, e.g., the spent purge gas stream comprises a dilute ethane stream. In an embodiment, the ethylene of the spent purge gas stream can be characterized by a partial pressure of from about 0.1 kPa to about 10 kPa, alternatively from about 0.5 kPa to about 8 kPa, or alternatively 1 kPa to about 5 kPa. In an embodiment, a portion of the ethane present in the spent purge gas stream can be adsorbed by the TSAC at the first temperature to yield TSAC-adsorbed ethane. In an embodiment, the loaded TSAC comprises TSAC-adsorbed ethane.

In some embodiments, the spent purge gas stream can be characterized by a ratio of a partial pressure for ethylene to a partial pressure for ethane of from about 1 to about 25, alternatively from about 1.5 to about 15, or alternatively from about 2 to about 10.

In an embodiment, the TSAC can selectively adsorb ethylene versus ethane. Without wishing to be limited by theory, an adsorption selectivity (S) of a first compound (e.g., a first hydrocarbon, such as for example ethylene) versus a second compound (e.g., a second hydrocarbon, such as for example ethane) for a given temperature can be calculated based on the following formula $S=(x_1/x_2)(y_2/y_1)$, wherein $x_1$ and $x_2$ are mole fractions in the adsorbed phase of the first compound and of the second compound, respectively, wherein $y_1$ and $y_2$ are mole fractions in the bulk or gas phase of the first compound and of the second compound, respectively, and wherein all mole fractions are given for the temperature at which the selectivity is being reported.

In an embodiment, the TSAC can be characterized by an adsorption selectivity of ethylene versus ethane at the first temperature of equal to or greater than about 5, alternatively greater than about 7, or alternatively greater than about 10.

In an embodiment, the non-adsorbed gas stream 520 can further comprise small amounts of ethylene (e.g., ethylene that was not adsorbed by the TSAC). As will be appreciated by one of skill in the art, and with the help of this disclosure, nitrogen and isobutane will not be adsorbed by the hydrocarbon adsorber of the TSAC, as such hydrocarbon adsorber is specifically chosen for selectively adsorbing ethylene. A small amount of ethane can be adsorbed by the hydrocarbon adsorber of the TSAC, however, as indicated by the adsorption selectivity of ethylene versus ethane of the TSAC, the amount of ethane adsorbed by the hydrocarbon adsorber is much lower than the amount of ethylene adsorbed by the hydrocarbon adsorber.

In an embodiment, the PEP process 2000 can generally comprise the step 2700 of heating the loaded TSAC to yield a regenerated TSAC. Heating the loaded TSAC can yield a regenerated TSAC and desorbed ethylene.

In an embodiment, at least a portion of the loaded TSAC can be heated to a second temperature to yield a regenerated TSAC, desorbed ethylene and desorbed ethane, wherein the desorbed ethylene comprises at least a portion of the TSAC-adsorbed ethylene, and wherein the desorbed ethane comprises at least a portion of the TSAC-adsorbed ethane. As will be appreciated by one of skill in the art, and with the help of this disclosure, depending on the value of the second temperature, it is unlikely that the entire amount of TSAC-adsorbed hydrocarbons (e.g., TSAC-adsorbed ethylene, TSAC-adsorbed ethane) will be desorbed during the regeneration step. Depending on the affinity of the hydrocarbons for the hydrocarbon adsorber, after a first TSAC cycle, some amount of hydrocarbons (e.g., ethylene, ethane) can remain adsorbed by the TSAC throughout further adsorption/regeneration cycles. As will be appreciated by one of skill in the art, and with the help of this disclosure, the TSACs can be calcined (e.g., heated to high temperatures, for example greater than about 300° C.) to remove residual adsorbed hydrocarbons and then returned into the PEP process.

In an embodiment, a molar ratio of desorbed ethylene to TSAC-adsorbed ethylene can be from about 0.01 to about 1, alternatively from about 0.1 to about 0.9, or alternatively from about 0.2 to about 0.8.

In an embodiment, a molar ratio of desorbed ethane to TSAC-adsorbed ethane can be from about 0 to about 1, alternatively from about 0.3 to about 0.9, or alternatively from about 0.4 to about 0.8.

In an embodiment, the loaded TSAC can be heated to the second temperature during the regeneration step by passing a heating fluid through at least a portion of the hollow tubes of the loaded TSAC.

In an embodiment, the PEP process 2000 can generally comprise the step 2800 of contacting the regenerated TSAC with a sweeping gas stream to yield a recovered adsorbed gas stream. Contacting the regenerated TSAC with a sweeping gas stream 510 (e.g., olefin-free isobutane) can yield a recovered adsorbed gas stream 530, wherein the sweeping gas sweeps away the desorbed ethylene. At least a portion of the recovered adsorbed gas stream 530 comprising ethylene can be pressurized and re-introduced 536 (e.g., as shown in FIG. 1) into a PEP process (e.g., into the slurry loop reactor system 100), for example via the reagents stream 110.

In an embodiment, the step of contacting the TSAC with a sweeping gas stream can occur prior to, concurrent with, or subsequent to the step of heating the loaded TSAC to yield a regenerated TSAC. In an embodiment, the step of contacting the TSAC with a sweeping gas stream and the step of heating the loaded TSAC to yield a regenerated TSAC can occur concurrently within the same TSA unit.

In an embodiment, a sweeping gas stream 510 can be communicated to the TSA unit 500 during a regeneration step to aid in the recovery of the adsorbed hydrocarbons. Without wishing to be limited by theory, the sweeping gas (e.g., olefin-free isobutane) generally flows through the open flow channels of the TSAC and carries away any desorbed hydrocarbons (e.g., desorbed ethylene, desorbed ethane) that it encounters in its path.

In an embodiment, the sweeping gas stream 510 can be heated to about the second temperature prior to being contacted with the TSAC.

In an embodiment, the recovered adsorbed gas stream 530 comprises sweeping gas, recovered ethylene and recovered ethane, wherein the recovered ethylene comprises at least a portion of the desorbed ethylene, and wherein the recovered ethane comprises at least a portion of the desorbed ethane. As will be appreciated by one of skill in the art, and with the help of this disclosure, the amount of ethane present in the recovered adsorbed gas stream is very low and its presence is due to a low amount of ethane being adsorbed by the TSAC. For purposes of the disclosure herein, the recovered adsorbed gas stream primarily contains a sweeping gas and ethylene. In an embodiment, the recovered adsorbed gas stream 530 comprises isobutane and ethylene 535. In an embodiment, a molar ratio of ethylene to ethane in the recovered adsorbed gas stream 530 can be equal to or greater than about 5, alternatively greater than about 7, or alternatively greater than about 10.

In an embodiment, the recovered adsorbed gas stream 530 can be optionally cooled in a heat exchanger and collected in a recycle diluent surge tank for feed to a reactor (e.g., reactor 104, reactor 106). In an embodiment, the isobutane and ethylene 535 can be pressurized (e.g., via one or more compressors) to yield a reintroduction stream 536 (e.g., as shown in FIG. 1) that can be recycled to the reagents stream 110. In some embodiments, the reintroduction stream 536 can be communicated to the purifier 102. As will be appreciated by one of skill in the art, and with the help of this disclosure, the amount of ethylene and isobutane present in the reintroduction stream 536 is dependent on a variety of factors, such as for example ethylene recovery rate, olefin-free isobutane flow rate (e.g., sweeping gas stream flow rate), ethylene concentration in the spent purge gas stream, etc.

In an embodiment, ethylene can be present in the reintroduction stream 536 in a range of from about 0.1 wt. % to about 50 wt. %, alternatively from about 0.5 wt. % to about 25 wt. %, or alternatively from about 1 wt. % to about 10 wt. %, by total weight of the reintroduction stream. In an embodiment, isobutane can be present in the reintroduction stream 536 in a range of from about 50 wt. % to about 99.9 wt. %, alternatively from about 75 wt. % to about 99.5 wt. %, or alternatively from about 90 wt. % to about 99 wt. %, by total weight of the reintroduction stream.

In an embodiment, a TSA unit comprises at least one TSAC disposed therein. In some embodiments, a TSA unit comprises a plurality of TSACs disposed therein.

In an embodiment, the TSA unit 500 as shown in FIG. 1 comprises at least two TSA units working in parallel. For example, the adsorption step (e.g., contacting the spent purge gas stream with the TSAC) occurs in a first temperature swing adsorption unit and the regeneration step (e.g., heating of the loaded TSAC and contacting the regenerated TSAC with a sweeping gas stream) occurs in a second temperature swing adsorption unit, wherein the first temperature swing adsorption unit and the second temperature swing adsorption unit are operated in parallel.

In some embodiments, the TSA unit comprises a single TSA unit, wherein both the adsorption step and the regeneration step occur in the same TSA unit. In such embodiments, the TSA unit can comprise moving beds (e.g., moving TSAC beds) that can separate gases (e.g., ethylene from ethane) in a single TSA unit with subsequent steps. As will be appreciated by one of skill in the art, and with the help of this disclosure, moving bed technologies require solid sorbent/adsorbent with superior stability and rapid regeneration. Further, as will be appreciated by one of skill in the art, and with the help of this disclosure, moving bed technologies typically use steam for the regeneration step.

In an embodiment, the PEP process 2000 can generally comprise the step 2900 of separating the non-adsorbed gas stream into a nitrogen stream and an isobutane and ethane stream. Referring to the embodiment of FIG. 1, a non-adsorbed gas stream 520 can be communicated from the TSA unit 500 to the INRU 600. Separating the non-adsorbed gas stream 520 into a nitrogen stream 610 and an isobutane and ethane stream 620 can be accomplished in the INRU 600. The nitrogen stream 610 can be recycled 616 to the purge column 400, for example via the purge gas stream 410. The isobutane and ethane stream 620 can be recycled 626 to the heavy distillation column 300, for example via the gas stream 210, according to the embodiments of the PEP system 1000 in FIG. 1.

In an embodiment, INRU 600 can comprise a membrane recovery unit, a pressure swing adsorption unit, a refrigeration unit, and the like. The INRU 600 can separate the non-adsorbed gas stream into the nitrogen stream 610 and the isobutane and ethane stream 620. At least a portion of the nitrogen 615 can be recycled 616 to the purge column 400, for example via the purge gas stream 410. Moreover, fresh nitrogen can be added to a nitrogen circuit comprising the purge gas stream 410 to account for nitrogen losses in the purge column 400, in the TSA unit 500 and/or in the INRU 600.

In an embodiment, the isobutane and ethane 625 can comprise isobutane, ethane, hexane and other heavy hydrocarbons. In some embodiments, at least a portion of the isobutane and ethane 625 can be recycled 626 to the heavy distillation column 300, for example via the gas stream 210. In other embodiments, at least a portion of the isobutane and ethane 625 can be optionally cooled in a heat exchanger and collected in a recycle diluent surge tank for feed to a reactor (e.g., reactor 104, reactor 106).

The various embodiments shown in the Figures can be simplified and may not illustrate common equipment such as heat exchangers, pumps, and compressors; however, a skilled artisan would recognize the disclosed processes and systems may include such equipment commonly used throughout polymer manufacturing.

A skilled artisan will recognize that industrial and commercial polyethylene manufacturing processes can necessitate one or more, often several, compressors or similar apparatuses. Such compressors are used throughout polyethylene manufacturing, for example to pressurize reactors 104, 106 during polymerization. Further, a skilled artisan will recognize that a polyethylene manufacturing process includes one or more deoxygenators and/or similar de-oxidizing apparatuses, for instance for purifying solvents or reactants and/or for purging reactors of oxygen. Because the infrastructure and the support therefore, for example to provide power and maintain the compressors and/or deoxygenators, already exists within a commercial polyethylene manufacturing plant, reallocating a portion of these available resources for use in the disclosed systems can necessitate little, if any, additional capital expenditure in order to incorporate the disclosed systems and or processes.

Further, because compressors, deoxygenators, and various other components are already employed in various polyethylene processes and systems, the opportunity for increased operation of such apparatuses can improve the overall efficiency of polyethylene production systems and processes. For example, when a portion of a PEP process or system is taken off-line for maintenance and/or repair, other portions of the system (e.g., a compressor, a deoxygenator, a reactor, etc.) can continue to provide service according to the current processes. Operating and/or reallocating resources for operation of the disclosed PEP systems and/or processes can thereby increase the efficiency with which conventional systems are used.

In an embodiment, a process for component (e.g., hydrocarbon) separation in a polymer production system can comprise the steps of (a) separating a polymerization product stream into a gas stream and a polymer stream, wherein the polymer stream comprises polyethylene, ethylene and ethane; (b) contacting at least a portion of the polymer stream with nitrogen to yield a purged polymer stream and a spent purge gas stream, wherein the purged polymer stream comprises polyethylene, and wherein the spent purge gas comprises nitrogen, ethylene, and ethane, wherein a pressure of the spent purge gas stream is from about 100 kPa to about 150 kPa, wherein ethylene is characterized by a partial pressure of less than about 10 kPa, and wherein ethane is characterized by a partial pressure of less than about 5 kPa; (c) contacting at least a portion of the spent purge gas stream with a TSAC comprising a 4 A zeolite and a plurality of hollow tubes at about 20° C. to yield a loaded TSAC and a non-adsorbed gas stream, wherein at least a portion of the ethylene is adsorbed by the TSAC to yield TSAC-adsorbed ethylene, wherein a portion of the ethane is adsorbed by the TSAC to yield TSAC-adsorbed ethane, wherein the loaded TSAC comprises TSAC-adsorbed ethylene and TSAC-adsorbed ethane, and wherein the TSAC is characterized by an adsorption selectivity of ethylene versus ethane at 20° C. of equal to or greater than about 5; (d) passing water at a temperature of about 50° C. through at least a portion of the hollow tubes of the loaded TSAC to yield a regenerated TSAC, desorbed ethylene and desorbed ethane, wherein the desorbed ethylene comprises at least a portion of the TSAC-adsorbed ethylene, and wherein the desorbed ethane comprises at least a portion of the TSAC-adsorbed ethane; and (e) contacting at least a portion of the 4 A zeolite of the regenerated TSAC with olefin-free isobutane to yield a recovered adsorbed gas stream comprising isobutane, recovered ethylene and recovered ethane, wherein the recovered ethylene comprises at least a portion of the desorbed ethylene, and wherein the recovered ethane comprises at least a portion of the desorbed ethane. In such embodiment, a cooling fluid comprising water can pass through at least a portion of the hollow tubes prior to and/or during (c) contacting the spent purge gas stream with the TSAC.

In an embodiment, a process for hydrocarbon recovery can comprise the steps of (a) providing a hydrocarbon stream comprising a first hydrocarbon and a second hydrocarbon, wherein the hydrocarbon stream is characterized by a pressure of from about 100 kPa to about 200 kPa, wherein the first hydrocarbon is characterized by a partial pressure of from about 1 kPa to about 20 kPa, and wherein the second hydrocarbon is characterized by a partial pressure of from about 0.1 kPa to about 10 kPa; (b) contacting at least a portion of the hydrocarbon stream with a TSAC to yield a loaded TSAC and a non-adsorbed gas stream, wherein at least a portion of the first hydrocarbon is adsorbed by the TSAC at a first temperature to yield TSAC-adsorbed first hydrocarbon, wherein a portion of the second hydrocarbon is adsorbed by the TSAC at the first temperature to yield TSAC-adsorbed second hydrocarbon, wherein the loaded TSAC comprises TSAC-adsorbed first hydrocarbon and TSAC-adsorbed second hydrocarbon, and wherein the TSAC is characterized by an adsorption selectivity of first hydrocarbon versus second hydrocarbon at the first temperature of equal to or greater than about 5; (c) heating at least a portion of the loaded TSAC to a second temperature to yield a regenerated TSAC, desorbed first hydrocarbon and desorbed second hydrocarbon, wherein the desorbed first hydrocarbon comprises at least a portion of the TSAC-adsorbed first hydrocarbon, wherein the desorbed second hydrocarbon comprises at least a portion of the TSAC-adsorbed second hydrocarbon, and wherein the second temperature is greater than the first temperature by equal to or greater than about 10° C.; and (d) contacting at least a portion of the regenerated TSAC with a sweeping gas stream to yield a recovered adsorbed gas stream, wherein the recovered adsorbed gas stream comprises a sweeping gas, recovered first hydrocarbon and recovered second hydrocarbon, wherein the recovered first hydrocarbon comprises at least a portion of the desorbed first hydrocarbon, and wherein the recovered second hydrocarbon comprises at least a portion of the desorbed second hydrocarbon. In such embodiment, the first hydrocarbon can comprise ethylene, the second hydrocarbon can comprise ethane, and the sweeping gas can comprise olefin-free isobutane.

In an embodiment, a TSAC system can comprise a TSA unit; wherein the temperature swing adsorption unit comprises at least one TSAC disposed therein; wherein the TSAC comprises a plurality of hollow tubes and a hydrocarbon adsorber, wherein the hollow tube comprises a hollow tube outer surface, wherein at least a portion of the hollow tube outer surface is in contact with the hydrocarbon adsorber; wherein the TSAC comprises a support, wherein the hydrocarbon adsorber contacts at least a portion of the support, is distributed throughout the support, or combinations thereof; wherein the temperature swing adsorption unit adsorbs at a first temperature, wherein the hydrocarbon adsorber adsorbs a first amount of a first hydrocarbon characterized by a first partial pressure and a second amount of a second hydrocarbon characterized by a second partial pressure to yield a loaded TSAC comprising a TSAC-adsorbed first hydrocarbon and a TSAC-adsorbed second hydrocarbon; wherein the hydrocarbon adsorber has an adsorption selectivity of the first hydrocarbon versus the second hydrocarbon at the first temperature of equal to or greater than about 5; wherein the temperature swing adsorption unit regenerates at a second temperature, wherein the loaded TSAC is regenerated to yield a regenerated TSAC, a third amount of a recovered first hydrocarbon and a fourth amount of a recovered second hydrocarbon; wherein the second temperature is greater than the first temperature by equal to or greater than about 10° C.; wherein a molar ratio of the third amount to the first amount at the first partial pressure is from about 0.01 to about 1; and wherein a molar ratio of the fourth amount at the second partial pressure to the second amount is from about 0 to about 1. In such embodiment, the first hydrocarbon can comprise ethylene, and the second hydrocarbon can comprise ethane.

In an embodiment, one or more of the disclosed systems (e.g., PEP system 1000) and/or processes (e.g., PEP process 2000) can advantageously display improvements in one or more system and/or process characteristics when compared to otherwise similar systems and/or processes lacking a step of ethylene recovery in a TSA unit. In an embodiment, the TSA unit as disclosed herein can advantageously allow for the recovery of a substantial portion of ethylene that would otherwise be lost due to conventional operation of such systems or processes, for example, by flaring. In an embodiment, one or more of the disclosed systems can allow for the recovery of up to about 75%, alternatively, up to about 85%, alternatively, up to about 90%, alternatively, up to about 95% by total weight of ethylene from a spent purge gas stream that would otherwise be lost. The recovery of such a portion of ethylene (e.g., unreacted ethylene monomers) can yield a significant economic benefit, for example, by improving the efficiency of usage of ethylene and decreasing capital inputs associated with the acquisition of ethylene.

In an embodiment, the TSA unit as disclosed herein can advantageously decrease the amount of ethane that is returned to a polymerization reactor (such as reactors 104 and/or 106) via a recycle stream (e.g., stream 536). By decreasing the amount of ethane contained in a stream to a polymerization reactor, the overall efficiency of the polyethylene production can be improved (for example, by increasing the ethylene concentration without reaching a bubble point in the loop reactor). For example, decreasing the amount of ethane in a stream can improve polymerization reactor efficiency, improve catalyst efficiency, reduce polymer fouling, reduce polymerization downtime, improve production of bimodal polymer types, improve production of copolymers, or combinations thereof.

In an embodiment, the TSA unit as disclosed herein can advantageously reduce a load on a compressor of the INRU due to a reduced gas stream throughput through such compressor. In some embodiments where the INRU comprises a pressure swing adsorption bed, such bed can advantageously display an increased capacity for isobutane adsorption, owing to the decreased content of ethylene in the gas stream entering the INRU. In other embodiments where the INRU comprises a membrane recovery unit, such membrane can advantageously display an increased throughput of isobutane, owing to the decreased content of ethylene in the gas stream entering the INRU. Additional advantages of the systems and/or processes for the production of a polyethylene polymer as disclosed herein can be apparent to one of skill in the art viewing this disclosure.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

ADDITIONAL DISCLOSURE

The following enumerated embodiments are provided as non-limiting examples.

A first embodiment which is a process for component separation in a polymer production system, comprising (a) separating a polymerization product stream into a gas stream and a polymer stream, wherein the polymer stream comprises polyethylene, ethylene and ethane; (b) contacting at least a portion of the polymer stream with a purge gas to yield a purged polymer stream and a spent purge gas stream, wherein the purged polymer stream comprises polyethylene, and wherein the spent purge gas comprises purge gas, ethylene, and ethane; (c) contacting at least a portion of the spent purge gas stream with a temperature swing adsorber contactor (TSAC) to yield a loaded TSAC and a non-adsorbed gas stream, wherein at least a portion of the ethylene is adsorbed by the TSAC at a first temperature to yield TSAC-adsorbed ethylene, wherein a portion of the ethane is adsorbed by the TSAC at the first temperature to yield TSAC-adsorbed ethane, and wherein the loaded TSAC comprises TSAC-adsorbed ethylene and TSAC-adsorbed ethane; (d) heating at least a portion of the loaded TSAC to a second temperature to yield a regenerated TSAC, desorbed ethylene and desorbed ethane, wherein the desorbed ethylene comprises at least a portion of the TSAC-adsorbed ethylene, and wherein the desorbed ethane comprises at least a portion of the TSAC-adsorbed ethane; and (e) contacting at least a portion of the regenerated TSAC with a sweeping gas stream to yield a recovered adsorbed gas stream, wherein the recovered adsorbed gas stream comprises sweeping gas, recovered ethylene and recovered ethane, wherein the recovered ethylene comprises at least a portion of the desorbed ethylene, and wherein the recovered ethane comprises at least a portion of the desorbed ethane.

A second embodiment which is the process of the first embodiment wherein the TSAC is characterized by an adsorption selectivity of ethylene versus ethane at the first temperature of equal to or greater than about 5.

A third embodiment which is the process of any of the first through second embodiments wherein the second temperature is greater than the first temperature by equal to or greater than about 10° C.

A fourth embodiment which is the process of any of the first through third embodiments wherein the ethylene of the spent purge gas stream is characterized by a partial pressure of from about 1 kPa to about 20 kPa.

A fifth embodiment which is the process of any of the first through fourth embodiments wherein the ethane of the spent purge gas stream is characterized by a partial pressure of from about 0.1 kPa to about 10 kPa.

A sixth embodiment which is the process of any of the first through fifth embodiments wherein a ratio of a partial pressure for ethylene to a partial pressure for ethane in the spent purge gas stream is from about 1 to about 25.

A seventh embodiment which is the process of any of the first through sixth embodiments wherein the spent purge gas stream is characterized by a pressure of from about 100 kPa to about 200 kPa.

An eighth embodiment which is the process of any of the first through seventh embodiments wherein the spent purge gas stream is further cooled to about the first temperature prior to (c) contacting at least a portion of the spent purge gas stream with the TSAC.

A ninth embodiment which is the process of any of the first through eighth embodiments wherein the first temperature is from about 10° C. to about 100° C.

A tenth embodiment which is the process of any of the first through ninth embodiments wherein the second temperature is from about 20° C. to about 200° C.

An eleventh embodiment which is the process of any of the first through tenth embodiments wherein a molar ratio of desorbed ethylene to TSAC-adsorbed ethylene is from about 0.01 to about 1.

A twelfth embodiment which is the process of any of the first through eleventh embodiments, wherein a molar ratio of desorbed ethane to TSAC-adsorbed ethane is from about 0 to about 1.

A thirteenth embodiment which is the process of any of the first through twelfth embodiments wherein at least a portion of the recovered adsorbed gas stream is recycled as a reagent for the polymer production system, wherein the recovered adsorbed gas stream comprises isobutane and ethylene.

A fourteenth embodiment which is the process of any of the first through thirteenth embodiments wherein at least a portion of the gas stream is distilled into a light distillation bottoms stream comprising olefin-free isobutane, wherein at least a portion of the light distillation bottoms stream is used as the sweeping gas stream for (e) contacting at least a portion of the regenerated TSAC.

A fifteenth embodiment which is the process of any of the first through fourteenth embodiments wherein at least a portion of the non-adsorbed gas stream is separated into a nitrogen stream and an isobutane and ethane stream.

A sixteenth embodiment which is the process of the fifteenth embodiment wherein at least a portion of the nitrogen stream is used as the purge gas for (b) contacting the polymer stream.

A seventeenth embodiment which is the process of any of the fifteenth through sixteenth embodiments wherein at least a portion of the isobutane and ethane stream is distilled into a light distillation bottoms stream comprising olefin-free isobutane.

An eighteenth embodiment which is the process of any of the first through seventeenth embodiments wherein (c) contacting the spent purge gas stream occurs in a first temperature swing adsorption unit and (d) heating of the loaded TSAC and (e) contacting the regenerated TSAC occurs in a second temperature swing adsorption unit, wherein the first temperature swing adsorption unit and the second temperature swing adsorption unit are operated in parallel.

A nineteenth embodiment which is the process of any of the first through eighteenth embodiments wherein (d) heating the loaded TSAC and (e) contacting the regenerated TSAC occur concurrently within the same temperature swing adsorption unit.

A twentieth embodiment which is the process of any of the first through nineteenth embodiments wherein the TSAC comprises a plurality of hollow tubes and a hydrocarbon adsorber, wherein the hollow tube comprises a hollow tube outer surface, wherein at least a portion of the hollow tube outer surface is in contact with the hydrocarbon adsorber.

A twenty-first embodiment which is the process of the twentieth embodiment wherein the hydrocarbon adsorber comprises a zeolite, metal-organic frameworks, carbon, molecular sieve carbon, zeolitic imidazolate frameworks, or combinations thereof.

A twenty-second embodiment which is the process of any of the twentieth through twenty-first embodiments wherein the hydrocarbon adsorber comprises a 4 Å molecular sieve.

A twenty-third embodiment which is the process of the twenty-first embodiment wherein the zeolite comprises a cationic zeolite, an aluminosilicate, an alkali metal aluminosilicate, a sodium aluminosilicate, an X zeolite, a NaX zeolite, a 13X zeolite, an A zeolite, a NaA zeolite, KA zeolite, NaCaA zeolite, or combinations thereof.

A twenty-fourth embodiment which is the process of the twentieth embodiment wherein the TSAC further comprises a support.

A twenty-fifth embodiment which is the process of any of the twentieth through twenty-fourth embodiments wherein the hydrocarbon adsorber contacts at least a portion of the support, is distributed throughout the support, or combinations thereof.

A twenty-sixth embodiment which is the process of any of the twenty-fourth through twenty-fifth embodiments wherein the support comprises a film, a foil, a mesh, a fiber cloth, a fiber cloth, a woven fiber mesh, a woven wire mesh, a metallic woven wire mesh, a polymeric membrane, a surface treated material, a surface treated metal foil, a woven fiber cloth, or combinations thereof.

A twenty-seventh embodiment which is the process of any of the twenty-fourth through twenty-sixth embodiments wherein the support comprises a thermally conductive polymer.

A twenty-eighth embodiment which is the process of any of the twenty-fourth through twenty-seventh embodiments wherein the support comprises cellulose acetate, polyvinylpyrrolidone, or combinations thereof.

A twenty-ninth embodiment which is the process of any of the twentieth through twenty-eighth embodiments wherein the hollow tubes comprise a thermally conductive material, a metal, aluminum, nickel, an alloy, stainless steel, thermally conductive polymers, polymeric materials, latexes, polyvinylidene chloride latex, carbon, glass, ceramics, or combinations thereof.

A thirtieth embodiment which is the process of any of the twentieth through twenty-ninth embodiments wherein the TSAC comprises a plurality of hollow fiber contactors.

A thirty-first embodiment which is the process of any of the twentieth through twenty-ninth embodiments wherein a cooling fluid passes through at least a portion of the hollow tubes prior to and/or during (c) contacting the spent purge gas stream with the TSAC.

A thirty-second embodiment which is the process of the thirty-first embodiment wherein the cooling fluid comprises water, tap water, process water, an aqueous solution, or combinations thereof.

A thirty-third embodiment which is the process of any of the twentieth through thirty-second embodiments wherein a heating fluid passes through at least a portion of the hollow tubes during (d) heating the loaded TSAC.

A thirty-fourth embodiment which is the process of any of the first through thirty-third embodiments wherein the heating fluid comprises warm water, hot water, steam, or combinations thereof.

A thirty-fifth embodiment which is the process of any of the first through thirty-fourth embodiments wherein the TSAC is characterized by a cycle time of from about 10 seconds to about 1 hour.

A thirty-sixth embodiment which is a process for component separation in a polymer production system, comprising (a) separating a polymerization product stream into a gas stream and a polymer stream, wherein the polymer stream comprises polyethylene, ethylene and ethane; (b) contacting at least a portion of the polymer stream with nitrogen to yield a purged polymer stream and a spent purge gas stream, wherein the purged polymer stream comprises polyethylene, and wherein the spent purge gas comprises nitrogen, ethylene, and ethane, wherein a pressure of the spent purge gas stream is from about 100 kPa to about 150 kPa, wherein ethylene is characterized by a partial pressure of less than about 10 kPa, and wherein ethane is characterized by a partial pressure of less than about 5 kPa; (c) contacting at least a portion of the spent purge gas stream with a temperature swing adsorber contactor (TSAC) comprising a 4 Å zeolite and a plurality of hollow tubes at about 20° C. to yield a loaded TSAC and a non-adsorbed gas stream, wherein at least a portion of the ethylene is adsorbed by the TSAC to yield TSAC-adsorbed ethylene, wherein a portion of the ethane is adsorbed by the TSAC to yield TSAC-adsorbed ethane, wherein the loaded TSAC comprises TSAC-adsorbed ethylene and TSAC-adsorbed ethane, and wherein the TSAC is characterized by an adsorption selectivity of ethylene versus ethane at 20° C. of equal to or greater than about 5; (d) passing water at a temperature of about 50° C. through at least a portion of the hollow tubes of the loaded TSAC to yield a regenerated TSAC, desorbed ethylene and desorbed ethane, wherein the desorbed ethylene comprises at least a portion of the TSAC-adsorbed ethylene, and wherein the desorbed ethane comprises at least a portion of the TSAC-adsorbed ethane; and (e) contacting at least a portion of the 4 A zeolite of the regenerated TSAC with olefin-free isobutane to yield a recovered adsorbed gas stream comprising isobutane, recovered ethylene and recovered ethane, wherein the recovered ethylene comprises at least a portion of the desorbed ethylene, and wherein the recovered ethane comprises at least a portion of the desorbed ethane.

A thirty-seventh embodiment which is the process of the thirty-sixth embodiment wherein a cooling fluid comprising water passes through at least a portion of the hollow tubes prior to and/or during (c) contacting the spent purge gas stream with the TSAC.

A thirty-eighth embodiment which is a process for component separation in a polymer production system, comprising (a) separating a polymerization product stream into a gas stream and a polymer stream, wherein the polymer stream comprises a polymer, a first hydrocarbon and a second hydrocarbon; (b) contacting at least a portion of the polymer stream with a purge gas to yield a purged polymer stream and a spent purge gas stream, wherein the purged polymer stream comprises the polymer, and wherein the spent purge gas comprises purge gas, the first hydrocarbon and the second hydrocarbon; (c) contacting at least a portion of the spent purge gas stream with a temperature swing adsorber contactor (TSAC) to yield a loaded TSAC and a non-adsorbed gas stream, wherein at least a portion of the first hydrocarbon is adsorbed by the TSAC at a first temperature to yield TSAC-adsorbed first hydrocarbon, wherein a portion of the second hydrocarbon is adsorbed by the TSAC at the first temperature to yield TSAC-adsorbed second hydrocarbon, wherein the loaded TSAC comprises TSAC-adsorbed first hydrocarbon and TSAC-adsorbed second hydrocarbon, and wherein the TSAC is characterized by an adsorption selectivity of first hydrocarbon versus second hydrocarbon at the first temperature of equal to or greater than about 5; (d) heating at least a portion of the loaded TSAC to a second temperature to yield a regenerated TSAC, desorbed first hydrocarbon and desorbed second hydrocarbon, wherein the desorbed first hydrocarbon comprises at least a portion of the TSAC-adsorbed first hydrocarbon, wherein the desorbed second hydrocarbon comprises at least a portion of the TSAC-adsorbed second hydrocarbon, and wherein the second temperature is greater than the first temperature by equal to or greater than about 10° C.; and (e) contacting at least a portion of the regenerated TSAC with a sweeping gas stream to yield a recovered adsorbed gas stream, wherein the recovered adsorbed gas stream comprises a sweeping gas, recovered first hydrocarbon and recovered second hydrocarbon, wherein the recovered first hydrocarbon comprises at least a portion of the desorbed first hydrocarbon, and wherein the recovered second hydrocarbon comprises at least a portion of the desorbed second hydrocarbon.

A thirty-ninth embodiment which is a process for hydrocarbon recovery, comprising (a) providing a hydrocarbon stream comprising a first hydrocarbon and a second hydrocarbon, wherein the hydrocarbon stream is characterized by a pressure of from about 100 kPa to about 200 kPa, wherein the first hydrocarbon is characterized by a partial pressure of from about 1 kPa to about 20 kPa, and wherein the second hydrocarbon is characterized by a partial pressure of from about 0.1 kPa to about 10 kPa; (b) contacting at least a portion of the hydrocarbon stream with a temperature swing adsorber contactor (TSAC) to yield a loaded TSAC and a non-adsorbed gas stream, wherein at least a portion of the first hydrocarbon is adsorbed by the TSAC at a first temperature to yield TSAC-adsorbed first hydrocarbon, wherein a portion of the second hydrocarbon is adsorbed by the TSAC at the first temperature to yield TSAC-adsorbed second hydrocarbon, wherein the loaded TSAC comprises TSAC-adsorbed first hydrocarbon and TSAC-adsorbed second hydrocarbon, and wherein the TSAC is characterized by an adsorption selectivity of first hydrocarbon versus second hydrocarbon at the first temperature of equal to or greater than about 5; (c) heating at least a portion of the loaded TSAC to a second temperature to yield a regenerated TSAC, desorbed first hydrocarbon and desorbed second hydrocarbon, wherein the desorbed first hydrocarbon comprises at least a portion of the TSAC-adsorbed first hydrocarbon, wherein the desorbed second hydrocarbon comprises at least a portion of the TSAC-adsorbed second hydrocarbon, and wherein the second temperature is greater than the first temperature by equal to or greater than about 10° C.; and (d) contacting at least a portion of the regenerated TSAC with a sweeping gas stream to yield a recovered adsorbed gas stream, wherein the recovered adsorbed gas stream comprises a sweeping gas, recovered first hydrocarbon and recovered second hydrocarbon, wherein the recovered first hydrocarbon comprises at least a portion of the desorbed first hydrocarbon, and wherein the recovered second hydrocarbon comprises at least a portion of the desorbed second hydrocarbon.

A fortieth embodiment which is a process for ethylene recovery from a dilute ethylene stream in a polyethylene production system, comprising (a) providing a dilute ethylene stream comprising ethylene and ethane, wherein a pressure of the dilute ethylene stream is from about 100 kPa to about 150 kPa, wherein ethylene is characterized by a partial pressure of less than about 10 kPa, and wherein ethane is characterized by a partial pressure of less than about 5 kPa; (b) contacting the dilute ethylene stream with a temperature swing adsorber contactor (TSAC) to yield a loaded TSAC and a non-adsorbed gas stream, wherein at least a portion of the ethylene is adsorbed by the TSAC at a first temperature to yield TSAC-adsorbed ethylene, wherein a portion of the ethane is adsorbed by the TSAC at the first temperature to yield TSAC-adsorbed ethane, wherein the loaded TSAC comprises TSAC-adsorbed ethylene and TSAC-adsorbed ethane, and wherein the TSAC is characterized by an adsorption selectivity of ethylene versus ethane at the first temperature of equal to or greater than about 5; (c) heating at least a portion of the loaded TSAC to a second temperature to yield a regenerated TSAC, desorbed ethylene and desorbed ethane, wherein the desorbed ethylene comprises at least a portion of the TSAC-adsorbed ethylene, wherein the desorbed ethane comprises at least a portion of the TSAC-adsorbed ethane, and wherein the second temperature is greater than the first temperature by equal to or greater than about 10° C.; and (d) contacting at least a portion of the regenerated TSAC with a sweeping gas stream to yield a recovered adsorbed gas stream, wherein the recovered adsorbed gas stream comprises a sweeping gas, recovered ethylene and recovered ethane, wherein the recovered ethylene comprises at least a portion of the desorbed ethylene, and wherein the recovered ethane comprises at least a portion of the desorbed ethane.

A forty-first embodiment which is a temperature swing adsorber contactor system comprising a temperature swing adsorption unit; wherein the temperature swing adsorption unit comprises at least one temperature swing adsorber contactor (TSAC) disposed therein; wherein the TSAC comprises a plurality of hollow tubes and a hydrocarbon adsorber, wherein the hollow tube comprises a hollow tube outer surface, wherein at least a portion of the hollow tube outer surface is in contact with the hydrocarbon adsorber; wherein the TSAC comprises a support, wherein the hydrocarbon adsorber contacts at least a portion of the support, is distributed throughout the support, or combinations thereof; wherein the temperature swing adsorption unit adsorbs at a first temperature, wherein the hydrocarbon adsorber adsorbs a first amount of a first hydrocarbon characterized by a first partial pressure and a second amount of a second hydrocarbon characterized by a second partial pressure to yield a loaded TSAC comprising a TSAC-adsorbed first hydrocarbon and a TSAC-adsorbed second hydrocarbon; wherein the hydrocarbon adsorber has an adsorption selectivity of the first hydrocarbon versus the second hydrocarbon at the first temperature of equal to or greater than about 5; wherein the temperature swing adsorption unit regenerates at a second temperature, wherein the loaded TSAC is regenerated to yield a regenerated TSAC, a third amount of a recovered first hydrocarbon and a fourth amount of a recovered second hydrocarbon; wherein the second temperature is greater than the first temperature by equal to or greater than about 10° C.; wherein a molar ratio of the third amount to the first amount at the first partial pressure is from about 0.01 to about 1; and wherein a molar ratio of the fourth amount at the second partial pressure to the second amount is from about 0 to about 1.

A forty-second embodiment which is a process for ethylene polymerization, comprising (a) polymerizing ethylene in a slurry loop reactor system to obtain a polymerization product stream; (b) separating a polymerization product stream in a flash chamber into a gas stream and a polymer stream comprising polyethylene, ethylene and ethane; (c) contacting at least a portion of the polymer stream with a purge gas in a purge column to yield a purged polymer stream and a spent purge gas stream, wherein the purged polymer stream comprises polyethylene, and wherein the spent purge gas comprises nitrogen, ethylene, and ethane; (d) contacting at least a portion of the spent purge gas stream with a temperature swing adsorber contactor (TSAC) to yield a loaded TSAC and a non-adsorbed gas stream, wherein at least a portion of the ethylene is adsorbed by the TSAC at a first temperature to yield TSAC-adsorbed ethylene, wherein a portion of the ethane is adsorbed by the TSAC at the first temperature to yield TSAC-adsorbed ethane, wherein the loaded TSAC comprises TSAC-adsorbed ethylene and TSAC-adsorbed ethane, and wherein the TSAC is characterized by an adsorption selectivity of ethylene versus ethane at the first temperature of equal to or greater than about 5; (e) heating at least a portion of the loaded TSAC to a second temperature to yield a regenerated TSAC, desorbed ethylene and desorbed ethane, wherein the desorbed ethylene comprises at least a portion of the TSAC-adsorbed ethylene, wherein the desorbed ethane comprises at least a portion of the TSAC-adsorbed ethane, and wherein the second temperature is greater than the first temperature by equal to or greater than about 10° C.; and (f) contacting at least a portion of the regenerated TSAC with olefin-free isobutane to yield a recovered adsorbed gas stream, wherein the recovered adsorbed gas stream comprises isobutane, recovered ethylene and recovered ethane, wherein the recovered ethylene comprises at least a portion of the desorbed ethylene, and wherein the recovered ethane comprises at least a portion of the desorbed ethane.

A forty-third embodiment which is the process of the forty-second embodiment, wherein at least a portion of the recovered adsorbed gas stream is recycled as a reagent for (a) polymerizing ethylene; wherein at least a portion of the non-adsorbed gas stream is separated into a nitrogen stream and an isobutane and ethane stream; wherein at least a portion of the nitrogen stream is used as the purge gas for (c) contacting the polymer stream; wherein at least a portion of the isobutane and ethane stream is distilled into a light distillation bottoms stream comprising olefin-free isobutane; and wherein at least a portion of the light distillation bottoms stream is used for (f) contacting the regenerated TSAC.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, ... 50 percent, 51 percent, 52 percent ... 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

We claim:

1. A process for component separation in a polymer production system, comprising:
   (a) separating a polymerization product stream into a gas stream and a polymer stream, wherein the gas stream comprises unreacted ethylene monomer, optional unreacted comonomer, and ethane;
   (b) processing at least a portion of the gas stream in one or more distillation columns to form a light hydrocarbon stream comprising ethylene and ethane;
   (c) contacting at least a portion of the light hydrocarbon stream with a temperature swing adsorber contactor (TSAC) to yield a loaded TSAC and a non-adsorbed gas stream, wherein at least a portion of the ethylene is adsorbed by the TSAC at a first temperature to yield TSAC-adsorbed ethylene, wherein a portion of the ethane is adsorbed by the TSAC at the first temperature to yield TSAC-adsorbed ethane, wherein the loaded TSAC comprises TSAC-adsorbed ethylene and TSAC-adsorbed ethane, and wherein the TSAC is characterized by an adsorption selectivity of ethylene versus ethane at the first temperature of equal to or greater than about 5;
   (d) heating at least a portion of the loaded TSAC to a second temperature to yield a regenerated TSAC, desorbed ethylene and desorbed ethane, wherein the desorbed ethylene comprises at least a portion of the TSAC-adsorbed ethylene, wherein the desorbed ethane comprises at least a portion of the TSAC-adsorbed ethane, wherein the second temperature is greater than the first temperature by equal to or greater than about 10° C., and wherein a molar ratio of desorbed ethylene to TSAC-adsorbed ethylene is from about 0.01 to about 1; and
   (e) contacting at least a portion of the regenerated TSAC with a sweeping gas stream to yield a recovered adsorbed gas stream, wherein the recovered adsorbed gas stream comprises sweeping gas, recovered ethylene and recovered ethane, wherein the recovered ethylene comprises at least a portion of the desorbed ethylene, and wherein the recovered ethane comprises at least a portion of the desorbed ethane.

2. The process of claim 1, wherein process step (d) of heating at least a portion of the loaded TSAC to a second temperature and process step (e) of contacting at least a portion of the regenerated TSAC with a sweeping gas stream occur concurrently.

3. The process of claim 1, wherein the TSAC comprises a plurality of hollow tubes and a hydrocarbon adsorber; wherein each hollow tube comprises a hollow tube outer surface; and wherein at least a portion of the hollow tube outer surface is in contact with the hydrocarbon adsorber.

4. The process of claim 3, wherein the hydrocarbon adsorber comprises a zeolite, metal-organic framework, carbon, molecular sieve carbon, zeolitic imidazolate framework, or combinations thereof.

5. The process of claim 1, wherein the TSAC is characterized by a cycle time of from about 10 seconds to about 1 hour.

6. The process of claim 3, wherein the TSAC further comprises a support, wherein the hydrocarbon adsorber contacts at least a portion of the support, is distributed throughout the support, or combinations thereof; wherein the support contacts at least a portion of the hollow tube outer surface, is distributed around the hollow tube, or combinations thereof; and wherein the support comprises a film, a foil, a mesh, a fiber cloth, a fiber cloth, a woven fiber mesh, a woven wire mesh, a metallic woven wire mesh, a polymeric membrane, a surface treated material, a surface treated metal foil, a woven fiber cloth, a thermally conductive polymer, a porous material, a porous thermally conductive polymer, a foamed material, a foamed thermally conductive polymer, or combinations thereof.

7. The process of claim 3, wherein the hollow tubes comprise a thermally conductive material, a metal, aluminum, nickel, an alloy, stainless steel, thermally conductive polymers, polymeric materials, latexes, polyvinylidene chloride latex, carbon, glass, ceramics, or combinations thereof.

8. The process of claim 3, wherein the TSAC comprises a spiral wound structure, wherein the hollow tubes are supported by at least one layer of the hydrocarbon adsorber.

9. The process of claim 8, wherein the at least one layer of the hydrocarbon adsorber and the hollow tubes supported by at least one layer of the hydrocarbon adsorber are wound around a mandrel.

10. The process of claim 8, wherein the hollow tubes are sandwiched between two surfaces of hydrocarbon adsorber and wherein the hollow tubes and the hydrocarbon adsorber are wound around a mandrel.

11. The process of claim 8, wherein the spiral wound structure is secured in a cylindrical geometry by a banding device.

12. The process of claim 3, wherein the TSAC comprises a stacked layered sheet structure.

13. The process of claim 3, wherein the TSAC comprises a plurality of hollow tubes in contact with an inner surface of a support layer, wherein an outer surface of the support layer is in contact with the hydrocarbon adsorber.

14. The process of claim 13, wherein the TSAC further comprises spacers, wherein the spacers are corrugations within the support, and wherein the spacers define open flow channels.

15. The process of claim 3, wherein the TSAC comprises a support in a corrugated form, wherein the support comprises folds.

16. The process of claim 15, wherein the hollow tubes occupy at least a portion of the folds.

17. The process of claim 3, wherein the TSAC comprises a support, wherein a portion of an inner surface of the support contacts the hollow tubes, wherein a portion of the inner surface of the support is coated with the hydrocarbon adsorber, wherein a portion of an outer surface of the hollow tubes is coated with the hydrocarbon adsorber, and wherein an outer surface of the support is not coated with the hydrocarbon adsorber.

18. The process of claim 3, wherein the TSAC comprises a plurality of hollow fiber contactors, wherein each hollow fiber contactor comprises a hollow tube, and a hydrocarbon adsorber dispersed throughout and supported within a porous polymer support; wherein the porous polymer support contacts at least a portion of an outer surface of the hollow tube; wherein a heat exchange fluid passes through the hollow tube; and wherein a sweeping gas flows across the hydrocarbon adsorber.

19. The process of claim 3, wherein the TSAC comprises a hollow fiber contactor comprising a hollow tube coating an inner surface of a hollow fiber, wherein the hollow fiber comprises a continuous polymer network, and wherein hydrocarbon adsorber particles are entrapped within the polymer network.

20. The process of claim 3, wherein the TSAC comprises a plurality of hollow fiber contactors; wherein each hollow fiber contactor comprises a hollow tube, a support and a hydrocarbon adsorber; wherein the hollow tube comprises a hollow tube outer surface; wherein at least a portion of the hollow tube outer surface is in contact with the hydrocarbon adsorber, the support, or both; wherein the hydrocarbon adsorber contacts at least a portion of the support, is distributed throughout the support, or combinations thereof; wherein each hollow fiber contactor has a cylindrical geometry; and wherein the hollow fiber contactors are bundled together, thereby creating open flow spaces between adjacent hollow fiber contactors.

21. The process of claim 1, wherein the polymer production system comprises at least two interconnected polymerization reactors.

22. The process of claim 21, wherein the at least two interconnected polymerization reactors comprise loop slurry reactors operated in series.

23. A process for ethylene polymerization, comprising:
 (a) polymerizing ethylene in a slurry loop reactor system to obtain a polymerization product stream;
 (b) separating the polymerization product stream in a flash chamber into a polymer stream and a gas stream comprising (i) ethylene, (ii) ethane, and optionally (iii) nitrogen, methane, propane, butane, isobutane, pentane, hexane, 1-hexene, heavier hydrocarbons, or combinations thereof;
 (c) distilling at least a portion of the gas stream in a heavy distillation column to form an intermediate hydrocarbon stream, a heavy distillation side stream, and a heavy distillation bottoms stream, wherein the intermediate hydrocarbon stream comprises (i) ethylene, (ii) ethane, and optionally (iii) nitrogen, methane, propane, butane, isobutane, or combinations thereof;
 (d) distilling at least a portion of the intermediate hydrocarbon stream in a light distillation column to form a light hydrocarbon stream comprising ethylene and ethane;
 (e) contacting at least a portion of the light hydrocarbon stream with a temperature swing adsorber contactor (TSAC) to yield a loaded TSAC and a non-adsorbed gas stream, wherein at least a portion of the ethylene is adsorbed by the TSAC at a first temperature to yield TSAC-adsorbed ethylene, wherein a portion of the ethane is adsorbed by the TSAC at the first temperature to yield TSAC-adsorbed ethane, wherein the loaded TSAC comprises TSAC-adsorbed ethylene and TSAC-adsorbed ethane, and wherein the TSAC is characterized by an adsorption selectivity of ethylene versus ethane at the first temperature of equal to or greater than about 5;

(f) heating at least a portion of the loaded TSAC to a second temperature to yield a regenerated TSAC, desorbed ethylene and desorbed ethane, wherein the desorbed ethylene comprises at least a portion of the TSAC-adsorbed ethylene, wherein the desorbed ethane comprises at least a portion of the TSAC-adsorbed ethane, and wherein the second temperature is greater than the first temperature by equal to or greater than about 10° C.; and (g) contacting at least a portion of the regenerated TSAC with olefin-free isobutane to yield a recovered adsorbed gas stream, wherein the recovered adsorbed gas stream comprises isobutane, recovered ethylene and recovered ethane, wherein the recovered ethylene comprises at least a portion of the desorbed ethylene, and wherein the recovered ethane comprises at least a portion of the desorbed ethane.

* * * * *